United States Patent
Ladunga et al.

(10) Patent No.: US 6,753,174 B2
(45) Date of Patent: Jun. 22, 2004

(54) ISOLATED HUMAN LACTATE DEHYDROGENASE PROTEINS

(75) Inventors: Steven I. Ladunga, Foster City, CA (US); Eugene Spier, Palo Alto, CA (US); Maureen Higgins, Bethesda, MD (US); Simon Greenberg, Foster City, CA (US); Yu Wang, Pittsburg, PA (US)

(73) Assignee: Applera Corporation, Norwalk, CT (US)

( * ) Notice: Subject to any disclaimer, the term of this patent is extended or adjusted under 35 U.S.C. 154(b) by 0 days.

(21) Appl. No.: 10/274,266

(22) Filed: Oct. 21, 2002

(65) Prior Publication Data

US 2003/0059893 A1 Mar. 27, 2003

Related U.S. Application Data

(62) Division of application No. 09/711,681, filed on Nov. 9, 2000, now Pat. No. 6,503,743.
(60) Provisional application No. 60/243,477, filed on Oct. 27, 2000.

(51) Int. Cl.[7] .............................. C12N 9/04; C12Q 1/32; A61K 38/44; C07K 17/00
(52) U.S. Cl. ........................ 435/190; 435/26; 424/944; 530/350
(58) Field of Search .................. 435/190, 26; 530/350; 424/94.4

(56) References Cited

U.S. PATENT DOCUMENTS

2002/0102604 A1 * 8/2002 Edwards et al.

OTHER PUBLICATIONS

Bougueleret et al., EMBL accession No. AAY36058, Jun. 24, 1999.*
Bergstein et al. "Isolation of two Novel WNT Genes, WNT14 and WNT15, one of Which (WNT15) is Closely Linked to WNT3 on Human Chromosome 17q21." Genomics, vol. 46, No. 3, Dec. 15, 1997. pp. 450–458.
George et al. "Current Methods in Sequence Comparison and Analysis." Macromolecular Sequencing and Synthesis Selected Methods and Applications. 1988. pp. 127–149.
Barton GJ. "Protein Sequence Alignment and Database Scanning." Protein Structure Prediction. A Practical Approach. 1996. pp. 31–63.

* cited by examiner

Primary Examiner—Rebecca E. Prouty
Assistant Examiner—Delia Ramirez
(74) Attorney, Agent, or Firm—Celera Genomics; Justin D. Karjala

(57) ABSTRACT

The present invention provides amino acid sequences of peptides that are encoded by genes within the human genome, the secreted peptides of the present invention. The present invention specifically provides isolated peptide and nucleic acid molecules, methods of identifying orthologs and paralogs of the secreted peptides, and methods of identifying modulators of the secreted peptides.

4 Claims, 5 Drawing Sheets

```
   1 ATGAGTTGGA CTGTGCCTGT TGTGCGGGCC AGCCAGAGAA TGAGCTCGGT
  51 GGGAGCGAAT TTCCTATGCC TGGGGATGGC CCTGTGTCTG CGTCAAGCAA
 101 CGCGCATCCC GCTAACGGC ACCTGGCTCT TCACACCCGT GAGCAAGATG
 151 GCGACTGTGA AGAGTGAGCT TATTGAGCGT TTCACTTCCG AGAAGCCCGT
 201 TCATCACAGT AAGGTCTCCA TCATAGGAAC TGGATCGGTG GGCATGGCCT
 251 GCGCTATCAG CATCTTATTA AAAGGCTTGA GTGATGAACT TGCCCTTGTG
 301 GATCTTGATG AAGACAAACT GAAGGGTGAG ACGATGGATC TTCAACATGG
 351 CAGCCCTTTC ACGAAAATGC CAAATATTGT TTGTAGCAAA GATTACTTTG
 401 TCACAGCAAA CTCCAACCTA GTGATTATCA CAGCAGGTGC ACGCCAAGAA
 451 AAGGGAGAAA CGCGCCTTAA TTTAGTCCAG CGAAATGTGG CCATCTTCAA
 501 GTTAATGATT TCCAGTATTG TCCAGTACAG CCCCCACTGC AAACTGATTA
 551 TTGTTTCCAA TCCAGTGGAT ATCTTAACTT ATGTAGCTTG GAAGTTGAGT
 601 GCATTTCCCA AAAACCGTAT TATTGGAAGC GGCTGTAATC TGGATACTGC
 651 TCGTTTTCGT TTCTTGATTG GACAAAAGCT TGGTATCCAT TCTGAAAGCT
 701 GCCATGGATG GATCCTCGGA GAGCATGGAG ACTCAAGTGT TCCTGTGTGG
 751 AGTGGAGTGA ACATAGCTGG TGTCCCTTTG AAGGATCTGA ACTCTGATAT
 801 AGGAACTGAT AAAGATCCTG AGCAATGGAA AAATGTCCAC AAAGAAGTGA
 851 CTGCAACTGC CTATGAGATT ATTAAAATGA AAGGTTATAC TTCTTGGGCC
 901 ATTGGCCTAT CTGTGGCCGA TTTAACAGAA AGTATTTTGA AGAATCTTAG
 951 GAGAATACAT CCAGTTTCCA CCATAACTAA GGGCCTCTAT GGAATAGATG
1001 AAGAAGTATT CCTCAGTATT CCTTGTATCC TGGGAGAGAA CGGTATTACC
1051 AACCTTATAA AGATAAAGCT GACCCCTGAA GAAGAGGCCC ATCTGAAAAA
1101 AAGTGCAAAA ACACTCTGGG AAATTCAGAA TAAGCTTAAG CTTTAA (SEQ ID NO:1)
```

FEATURES:
Start codon: 1
Stop codon: 1144

Homologous proteins:
Top 10 BLAST Hits

| | Score | E |
|---|---|---|
| gi\|6754524\|ref\|NP_034829.1\| lactate dehydrogenase 1, A chain >g... | 513 | e-144 |
| gi\|65923\|pir\|\|DEMSLM L-lactate dehydrogenase (EC 1.1.1.27) chai... | 512 | e-144 |
| gi\|5199139\|gb\|AAD40733.1\|AF070996_1 (AF070996) lactate dehydrog... | 508 | e-143 |
| gi\|1170740\|sp\|P00339\|LDHM_PIG L-LACTATE DEHYDROGENASE M CHAIN (... | 508 | e-143 |
| gi\|65924\|pir\|\|DEPGLM L-lactate dehydrogenase (EC 1.1.1.27) chai... | 506 | e-142 |
| gi\|443576\|pdb\|9LDT\|A Chain A, Lactate Dehydrogenase (E.C.1.1.1.... | 506 | e-142 |
| gi\|8393706\|ref\|NP_058721.1\| lactate dehydrogenase A >gi\|126051\|... | 506 | e-142 |
| gi\|126050\|sp\|P13491\|LDHM_RABIT L-LACTATE DEHYDROGENASE M CHAIN ... | 504 | e-142 |
| gi\|5031857\|ref\|NP_005557.1\| lactate dehydrogenase A >gi\|126047\|... | 503 | e-141 |
| gi\|126045\|sp\|P19858\|LDHM_BOVIN L-LACTATE DEHYDROGENASE M CHAIN ... | 501 | e-141 |

EST:
| | | |
|---|---|---|
| CRA\|114000006539936 /altid=gi\|8143724 /dataset=dbest /taxon=960... | 965 | 0.0 |
| CRA\|3000001750954 /altid=gi\|2051275 /dataset=dbest /taxon=9606 ... | 946 | 0.0 |
| CRA\|3000001788928 /altid=gi\|2115221 /dataset=dbest /taxon=9606 ... | 541 | e-151 |
| CRA\|1000486586422 /altid=gi\|4736297 /dataset=dbest /taxon=9606 ... | 141 | 3e-31 |

FIGURE 1A

```
  1 MSWTVPVVRA SQRMSSVGAN FLCLGMALCL RQATRIPLNG TWLFTPVSKM
 51 ATVKSELIER FTSEKPVHHS KVSIIGTGSV GMACAISILL KGLSDELALV
101 DLDEDKLKGE TMDLQHGSPF TKMPNIVCSK DYFVTANSNL VIITAGARQE
151 KGETRLNLVQ RNVAIFKLMI SSIVQYSPHC KLIIVSNPVD ILTYVAWKLS
201 AFPKNRIIGS GCNLDTARFR FLIGQKLGIH SESCHGWILG EHGDSSVPVW
251 SGVNIAGVPL KDLNSDIGTD KDPEQWKNVH KEVTATAYEI IKMKGYTSWA
301 IGLSVADLTE SILKNLRRIH PVSTITKGLY GIDEEVFLSI PCILGENGIT
351 NLIKIKLTPE EEAHLKKSAK TLWEIQNKLK L (SEQ ID NO:2)
```

FEATURES:
Functional domains and key regions:

| InterPro | Results of FPrintScan vs. PRINTS | Results of HMMPfam vs. PFAM-A | Results of ScanProsite vs. PROSITE | Results of ProfileScan vs. PROFILES | Results of BlastProDom vs. PRODOM |
|---|---|---|---|---|---|
| IPR000205 NAD binding site | | | | PS50205 [72-102] | |
| IPR000594 UBA/THIF-type NAD/FAD binding fold | | | | PS50204 [62-103] | |
| IPR001236 Lactate/malate dehydrogenase | | PF00056 [71-380] | | | |
| IPR001557 L-lactate dehydrogenase | PR00086 [71-95] [96-120] [183-203] [207-225] [237-250] | | PS00064 [239-245] | | |

FIGURE 2A

BLAST Alignment to Top Hit:
```
>gi|6754524|ref|NP_034829.1| lactate dehydrogenase 1, A chain
    >gi|126048|sp|P06151|LDHM_MOUSE L-LACTATE DEHYDROGENASE M
    CHAIN (LDH-A) >gi|535924|emb|CAA68410.1| (Y00309) LDH-A
    [Mus musculus] >gi|538135|gb|AAA21466.1| (U13687) lactate
    dehydrogenase-A [Mus musculus]
    >gi|1200099|emb|CAA26360.1| (X02520) lactate
    dehydrogenase [Mus musculus]
    Length = 332

Score =  513 bits (1307), Expect = e-144
 Identities = 239/331 (72%), Positives = 290/331 (87%)
 Frame = +1

Query: 148   MATVKSELIERFTSEKPVHHSKVSIIGTGSVGMACAISILLKGLSDELALVDLDEDKLKG 327
             MAT+K +LI    E+    +K++++G G+VGMACAISIL+K L+DELALVD+ EDKLKG
Sbjct: 1     MATLKDQLIVNLLKEEQAPQNKITVVGVGAVGMACAISILMKDLADELALVDVMEDKLKG 60

Query: 328   ETMDLQHGSPFTKMPNIVCSKDYFVTANSNLVIITAGARQEKGETRLNLVQRNVAIFKLM 507
             E MDLQHGS F K P IV SKDY VTANS LVIITAGARQ++GE+RLNLVQRNV IFK +
Sbjct: 61    EMMDLQHGSLFLKTPKIVSSKDYCVTANSKLVIITAGARQQEGESRLNLVQRNVNIFKFI 120

Query: 508   ISSIVQYSPHCKLIIVSNPVDILTYVAWKLSAFPKNRIIGSGCNLDTARFRFLIGQKLGI 687
             I +IV+YSPHCKL+IVSNPVDILTYVAWK+S FPKNR+IGSGCNLD+ARFR+L+G++LG+
Sbjct: 121   IPNIVKYSPHCKLLIVSNPVDILTYVAWKISGFPKNRVIGSGCNLDSARFRYLMGERLGV 180

Query: 688   HSESCHGWILGEHGDSSVPVWSGVNIAGVPLKDLNSDIGTDKDPEQWKNVHKEVTATAYE 867
             H+ SCHGW+LGEHGDSSVPVWSGVN+AGV LK LN ++GTD D EQWK VHK+V  +AYE
Sbjct: 181   HALSCHGWVLGEHGDSSVPVWSGVNVAGVSLKSLNPELGTDADKEQWKEVHKQVVDSAYE 240

Query: 868   IIKMKGYTSWAIGLSVADLTESILKNLRRIHPVSTITKGLYGIDEEVFLSIPCILGENGI 1047
             +IK+KGYTSWAIGLSVADL ESI+KNLRR+HP+ST+ KGLYGI+E+VFLS+PCILG+NGI
Sbjct: 241   VIKLKGYTSWAIGLSVADLAESIMKNLRRVHPISTMIKGLYGINEDVFLSVPCILGQNGI 300

Query: 1048  TNLIKIKLTPEEEAHLKKSAKTLWEIQNKLK 1140
             +++ K+ LTPEEEA LKKSA TLW IQ +L+
Sbjct: 301   SDVVKVTLTPEEEARLKKSADTLWGIQKELQ 331 (SEQ ID NO:4)
```

Hmmer results:

| Model | Description | Score | E-value | N |
|---|---|---|---|---|
| PF00056 | lactate/malate dehydrogenase | 543.3 | 1.7e-159 | 1 |
| PF00389 | D-isomer specific 2-hydroxyacid dehydrogenas | 2.3 | 1.3 | 1 |

Parsed for domains:

| Model | Domain | seq-f | seq-t | hmm-f | hmm-t | score | E-value |
|---|---|---|---|---|---|---|---|
| PF00389 | 1/1 | 67 | 89 .. | 68 | 90 .. | 2.3 | 1.3 |
| PF00056 | 1/1 | 71 | 380 .. | 1 | 331 [] | 543.3 | 1.7e-159 |

FIGURE 2B

```
   1 CAGAAGTGGT ATCAAAGTTG CACCAATCTG GCCAGAAACT CATGCTCAGA
  51 TACTCTGTTT AACAAGAGAT CAGCTGGGAT GATGGATGAG ACCAGGGGAT
 101 TTCCATAGCA CTAGGAAGTC CCCAAGACCA CGACCTCAAC TTAACTTTTT
 151 TATCATCAGC AGCCCCACAC AGCCTGGCAT CCAGTAGGCA CCCAATACTG
 201 ATGGGCTTTA TAAGAACACC AAAAGTGCAC TCTGGGCCTT GATTTATACT
 251 ACCAGTAGGC ATGGGGAGAC AAGGAATGCC AGTCTGTGAT TCCAGCAAGA
 301 GGCAAGACGA AAATCCATTT ATTCAGCAGC TAATACATGT AGCAGGGTGA
 351 TTCATTTTCC AAAAATATGC AGTAGTATGC TGAGATTTAG TGCTGGAGTG
 401 ACTCCCAGCC GGCCCCTACC CTGCTGAAGC CCCAGCCGAC TGTCCCAGGG
 451 TGGGTCCTGG CCAGGACTGG CACCAAGGCA GTGGAATCCT TTCAAAATAG
 501 GCCTCCAGCG CCATAGACCA GAAAGCAGGC GCCCAATTCT GGGACACTGG
 551 GAGATGGTGC AGGCAGCCAC CAGTATGCAA AGCATAGAGC CCTATCCTTC
 601 CTGGCAGGGT CACGGTTCAG AAAACGTAAC CTTATTTTCA TCTGTAGTTA
 651 ACAGAAGCAT GTTTCCTCAG CATTCATATT AAAAATAAAA AACTAGTAAT
 701 TCCAGGGATC TCGGTTAGCC TCTTAAGCAT GTCAACTATT GATAATACTC
 751 TTAGCAAAAC TAACTCCAGA AATCACTTGC TAGAGAAGCA GCCCTTCACT
 801 GCCTTAGTCT GAGCACCCAC GGAAAGCACG TGTTGGAGAC TCTGGCAAGG
 851 CCCGCGCAGC CGCAGTAGAG GGCCAGGGGG CGGGGCACGC GCACCTGCCG
 901 TAGAGTGCTG AAGGTCCTGC CAACGGCTCT CTTGGCGTCT CAACGTTCGG
 951 ATCAGCAGCT TTTTTCCATT CTCTCTCTCC ACTTCTTCAG TGAGCAGCCA
1001 TGAGTTGGAC TGTGCCTGTT GTGCGGGCCA GCCAGAGAAT GAGCTCGGTG
1051 GGAGCGAATT TCCTATGCCT GGGGATGGCC CTGTGTCTGC GTCAAGCAAC
1101 GCGCATCCCG CTCAACGGCA CCTGGCTCTT CACACCCGTG AGCAAGATGG
1151 CGACTGTGAA GAGTGAGCTT ATTGAGCGTT TCACTTCCGA GAAGCCCGTT
1201 CATCACAGTA AGGTCTCCAT CATAGGAACT GGATCGGTGG GCATGGCCTG
1251 CGCTATCAGC ATCTTATTAA AAGGCTTGAG TGATGAACTT GCCCTTGTGG
1301 ATCTTGATGA AGACAAACTG AAGGGTGAGA CGATGGATCT TCAACATGGC
1351 AGCCCTTTCA CGAAAATGCC AAATATTGTT TGTAGCAAAG ATTACTTTGT
1401 CACAGCAAAC TCCAACCTAG TGATTATCAC AGCAGGTGCA CGCCAAGAAA
1451 AGGGAGAAAC GCGCCTTAAT TTAGTCCAGC GAAATGTGGC CATCTTCAAG
1501 TTAATGATTT CCAGTATTGT CCAGTACAGC CCCCACTGCA AACTGATTAT
1551 TGTTTCCAAT CCAGTGGATA TCTTAACTTA TGTAGCTTGG AAGTTGAGTG
1601 CATTTCCCAA AAACCGTATT ATTGGAAGCG GCTGTAATCT GGATACTGCT
1651 CGTTTCGTT TCTTGATTGG ACAAAAGCTT GGTATCCATT CTGAAAGCTG
1701 CCATGGATGG ATCCTCGGAG AGCATGGAGA CTCAAGTGTT CCTGTGTGGA
1751 GTGGAGTGAA CATAGCTGGT GTCCCTTTGA AGGATCTGAA CTCTGATATA
1801 GGAACTGATA AAGAACCTGA GCAATGGAAA AATGTCCACA AGAAGTGAC
1851 TGCAACTGCC TATGAGATTA TTAAAATGAA AGGTTATACT TCTTGGGCCA
1901 TTGGCCTATC TGTGGCCGAT TTAACAGAAA GTATTTTGAA GAATCTTAGG
1951 AGAATACATC CAGTTTCCAC CATAACTAAG GGCCTCTATG GAATAGATGA
2001 AGAAGTATTC CTCAGTATTC CTTGTATCCT GGGAGAGAAC GGTATTACCA
2051 ACCTTATAAA GATAAAGCTG ACCCCTGAAG AAGAGGCCCA TCTGAAAAAA
2101 AGTGCAAAAA CACTCTGGGA AATTCAGAAT AAGCTTAAGC TTTAAAGTTG
2151 CCTAAAACTA CCATTCCGAA ATTATTGAAG AGATCATAGA TACAGGATTA
2201 TATAACGAAA TTTTGAATAA ACTTGAATTC CTAAAAGATG AAACAGGAA
2251 AGTAGGTAGA GTGATTTTCC TATTTATTTA GTCCTCCAGC TCTTTTATTG
2301 AGCATCCACG TGCTGGACGA TACTTATTTA CAATTCCTAA GTATTTTTGG
2351 TACCTCTGAT GTAGCAGCAC TTGCCATGTT ATATATATGT AGTTGGCATT
2401 TGGTTCCCAA AAAGTAGGAT GTAGGTATTT ATTGTGTTCC AGAAATTCCG
2451 ACTCTTTTCA TTAGATATAT GCTATTTCTT TCATTCTTGC TGGTTTATAC
2501 CTATGTTCAT TTATATGCTG TAAAAAAGTA GTAGCTTCTT CTACAATGTA
2551 AAAATAAATG TACATACAAA AAAATGCAGT AGTATATACA ATCTTTTGTT
2601 TTGCTTCCTT TGATAGTTAA TAAATTCCGT TTGTTGAATC AATAAAATAC
2651 GGCGAGCCAT ATGATTTGCT TCATGAGAAA CCAGATCACA AACCCAAAGG
2701 CTTAAAACAG ATAGACATTA AAATGGATAT TGGCCATACC TTCCCAGCAT
2751 AATGATGAAT GATGAAGCCT TGGTTCCAAC TGTTGAAGTG CTCATGACTC
2801 CCAATCTGCA TCTGAAGTTT CTGGAGCAGC GTCTGATCTG CCCCCTCACC
2851 CACCGCATGC ATCGTGGCGC ACACGTCATC CAGGATGCTC ATGATGCCAG
2901 GAGGGTTCTG ATGGGAGCAA GAAGGCAAGG CCCTAGTCAC TGACCTCTCC
2951 AAAACAGACA ATGCTTATCA GGTCCTTTCT TAGGCAAGGA AACAGCTCCC
```

FIGURE 3A

```
3001  CAGACTTAAG ATACCATCTT GAAAGTCAGT ATTCCCCTTC AGGCAAGAAT
3051  GCAATTAATA GTCCCAAATA GGGAGTCACC ACTTAGATCT AAAGAGGGAG
3101  GAAACTCCAC TTTCCAAAAA GCTGTTTAAC TCCCTGAAGT TTTA (SEQ ID NO:3)
```

FEATURES:

Start:1000
Exon: 1000-2145
Stop: 2143

Map data:

chr. 15

FIGURE 3B

SEQUENCE LISTING

<160> NUMBER OF SEQ ID NOS: 4

<210> SEQ ID NO 1
<211> LENGTH: 1146
<212> TYPE: DNA
<213> ORGANISM: Homo sapiens

<400> SEQUENCE: 1

```
atgagttgga ctgtgcctgt tgtgcgggcc agccagagaa tgagctcggt gggagcgaat      60
ttcctatgcc tggggatggc cctgtgtctg cgtcaagcaa cgcgcatccc gctcaacggc     120
acctggctct tcacacccgt gagcaagatg gcgactgtga agagtgagct tattgagcgt     180
ttcacttccg agaagcccgt tcatcacagt aaggtctcca tcataggaac tggatcggtg     240
ggcatggcct gcgctatcag catcttatta aaaggcttga gtgatgaact tgcccttgtg     300
gatcttgatg aagacaaact gaagggtgag acgatggatc ttcaacatgg cagcccttc      360 acgaaaatgc caaatattgt ttgtagcaaa gattactttg tcacagcaaa ctccaaccta     420
gtgattatca cagcaggtgc acgccaagaa aagggagaaa cgcgccttaa tttagtccag     480
cgaaatgtgg ccatcttcaa gttaatgatt tccagtattg tccagtacag cccccactgc     540
aaactgatta ttgtttccaa tccagtggat atcttaactt atgtagcttg gaagttgagt     600
gcatttccca aaaccgtat tattggaagc ggctgtaatc tggatactgc tcgttttcgt      660
ttcttgattg gacaaaagct tggtatccat tctgaaagct gccatggatg gatcctcgga     720
gagcatggag actcaagtgt tcctgtgtgg agtggagtga acatagctgg tgtcccttg      780 aaggatctga actctgatat aggaactgat aaagatcctg agcaatggaa aaatgtccac     840
```

```
aaagaagtga ctgcaactgc ctatgagatt attaaaatga aaggttatac ttcttgggcc    900
attggcctat ctgtggccga tttaacagaa agtatttga agaatcttag gagaatacat    960
ccagtttcca ccataactaa gggcctctat ggaatagatg aagaagtatt cctcagtatt   1020
ccttgtatcc tgggagagaa cggtattacc aaccttataa agataaagct gaccccctgaa   1080 gaagaggccc atctgaaaaa aagtgcaaaa acactctggg aaattcagaa taagcttaag   1140
ctttaa                                                              1146
```

<210> SEQ ID NO 2
<211> LENGTH: 381
<212> TYPE: PRT
<213> ORGANISM: Homo sapiens

<400> SEQUENCE: 2

```
Met Ser Trp Thr Val Pro Val Val Arg Ala Ser Gln Arg Met Ser Ser
 1               5                  10                  15

Val Gly Ala Asn Phe Leu Cys Leu Gly Met Ala Leu Cys Leu Arg Gln
                20                  25                  30

Ala Thr Arg Ile Pro Leu Asn Gly Thr Trp Leu Phe Thr Pro Val Ser
            35                  40                  45

Lys Met Ala Thr Val Lys Ser Glu Leu Ile Glu Arg Phe Thr Ser Glu
    50                  55                  60

Lys Pro Val His His Ser Lys Val Ser Ile Ile Gly Thr Gly Ser Val
 65                  70                  75                  80

Gly Met Ala Cys Ala Ile Ser Ile Leu Leu Lys Gly Leu Ser Asp Glu
                85                  90                  95

Leu Ala Leu Val Asp Leu Asp Glu Asp Lys Leu Lys Gly Glu Thr Met
               100                 105                 110

Asp Leu Gln His Gly Ser Pro Phe Thr Lys Met Pro Asn Ile Val Cys
           115                 120                 125

Ser Lys Asp Tyr Phe Val Thr Ala Asn Ser Asn Leu Val Ile Ile Thr
    130                 135                 140

Ala Gly Ala Arg Gln Glu Lys Gly Glu Thr Arg Leu Asn Leu Val Gln
145                 150                 155                 160

Arg Asn Val Ala Ile Phe Lys Leu Met Ile Ser Ser Ile Val Gln Tyr
                165                 170                 175

Ser Pro His Cys Lys Leu Ile Ile Val Ser Asn Pro Val Asp Ile Leu
            180                 185                 190

Thr Tyr Val Ala Trp Lys Leu Ser Ala Phe Pro Lys Asn Arg Ile Ile
    195                 200                 205

Gly Ser Gly Cys Asn Leu Asp Thr Ala Arg Phe Arg Phe Leu Ile Gly
210                 215                 220

Gln Lys Leu Gly Ile His Ser Glu Ser Cys His Gly Trp Ile Leu Gly
225                 230                 235                 240

Glu His Gly Asp Ser Ser Val Pro Val Trp Ser Gly Val Asn Ile Ala
                245                 250                 255

Gly Val Pro Leu Lys Asp Leu Asn Ser Asp Ile Gly Thr Asp Lys Asp
            260                 265                 270

Pro Glu Gln Trp Lys Asn Val His Lys Glu Val Thr Ala Thr Ala Tyr
    275                 280                 285

Glu Ile Ile Lys Met Lys Gly Tyr Thr Ser Trp Ala Ile Gly Leu Ser
    290                 295                 300

Val Ala Asp Leu Thr Glu Ser Ile Leu Lys Asn Leu Arg Arg Ile His
```

```
305                 310                 315                 320
Pro Val Ser Thr Ile Thr Lys Gly Leu Tyr Gly Ile Asp Glu Val
                325                 330                 335
Phe Leu Ser Ile Pro Cys Ile Leu Gly Glu Asn Gly Ile Thr Asn Leu
            340                 345                 350
Ile Lys Ile Lys Leu Thr Pro Glu Glu Glu Ala His Leu Lys Lys Ser
        355                 360                 365
Ala Lys Thr Leu Trp Glu Ile Gln Asn Lys Leu Lys Leu
    370                 375                 380

<210> SEQ ID NO 3
<211> LENGTH: 3144
<212> TYPE: DNA
<213> ORGANISM: Homo sapiens

<400> SEQUENCE: 3
cagaagtggt atcaaagttg caccaatctg ccagaaact  catgctcaga tactctgttt     60
aacaagagat cagctgggat gatggatgag accaggggat tccatagca ctaggaagtc    120
cccaagacca cgacctcaac ttaactttt  tatcatcagc agcccacac  agcctggcat    180
ccagtaggca cccaatactg atgggcttta taagaacacc aaaagtgcac tctgggcctt    240
gatttatact accagtaggc atggggagac aaggaatgcc agtctgtgat tccagcaaga    300
ggcaagacga aaatccattt attcagcagc taatacatgt agcagggtga ttcattttcc    360
aaaaatatgc agtagtatgc tgagatttag tgctggagtg actcccagcc ggcccctacc    420
ctgctgaagc cccagccgac tgtcccaggg tgggtcctgg ccaggactgg caccaaggca    480
gtggaatcct ttcaaaatag gcctccagcg ccatagacca gaaagcaggc gcccaattct    540
gggacactgg gagatggtgc aggcagccac cagtatgcaa agcatagagc cctatccttc    600
ctggcagggt cacggttcag aaacgtaac  cttatttca  tctgtagtta acagaagcat    660
gtttcctcag cattcatatt aaaaataaaa aactagtaat tccagggatc tcggttagcc    720
tcttaagcat gtcaactatt gataatactc ttagcaaaac taactccaga atcacttgc    780
tagagaagca gcccttcact gccttagtct gagcacccac ggaaagcacg tgttggagac    840
tctggcaagg cccgcgcagc cgcagtagag ggccagggggg cggggcacgc gcacctgccg    900
tagagtgctg aaggtcctgc caacggctct cttggcgtct caacgttcgg atcagcagct    960
tttttccatt ctctctctcc acttcttcag tgagcagcca tgagttggac tgtgcctgtt   1020
gtgcgggcca gccagagaat gagctcggtg ggagcgaatt cctatgcct  ggggatggcc   1080
ctgtgtctgc gtcaagcaac gcgcatcccg ctcaacggca cctggctctt cacacccgtg   1140
agcaagatgg cgactgtgaa gagtgagctt attgagcgtt tcacttccga aagcccgtt    1200
catcacagta aggtctccat cataggaact ggatcggtgg gcatggcctg cgctatcagc   1260
atcttattaa aaggcttgag tgatgaactt gcccttgtgg atcttgatga agacaaactg   1320
aagggtgaga cgatggatct tcaacatggc agccctttca cgaaaatgcc aaatattgtt   1380
tgtagcaaag attactttgt cacagcaaac tccaacctag tgattatcac agcaggtgca   1440
cgccaagaaa agggagaaac gcgccttaat ttagtccagc gaaatgtggc catcttcaag   1500
ttaatgattt ccagtattgt ccagtacagc ccccactgca aactgattat tgtttccaat   1560
ccagtggata tcttaactta tgtagcttgg aagttgagtg catttcccaa aaaccgtatt   1620
attggaagcg gctgtaatct ggatactgct cgttttcgtt tcttgattgg acaaaagctt   1680
ggtatccatt ctgaaagctg ccatggatgg atcctcggag agcatggaga ctcaagtgtt   1740
```

-continued

```
cctgtgtgga gtggagtgaa catagctggt gtcccttttga aggatctgaa ctctgatata    1800
ggaactgata aagatcctga gcaatggaaa aatgtccaca agaagtgac tgcaactgcc      1860
tatgagatta ttaaaatgaa aggttatact tcttgggcca ttggcctatc tgtggccgat    1920
ttaacagaaa gtattttgaa gaatcttagg agaatacatc cagtttccac cataactaag    1980
ggcctctatg gaatagatga agaagtattc ctcagtattc cttgtatcct gggagagaac    2040
ggtattacca accttataaa gataaagctg accccctgaag aagaggccca tctgaaaaaa   2100
agtgcaaaaa cactctggga aattcagaat aagcttaagc tttaaagttg cctaaaacta    2160
ccattccgaa attattgaag agatcataga tacaggatta tataacgaaa ttttgaataa    2220
acttgaattc ctaaaagatg gaaacaggaa agtaggtaga gtgattttcc tatttattta    2280
gtcctccagc tctttttattg agcatccacg tgctggacga tacttattta caattcctaa   2340
gtatttttgg tacctctgat gtagcagcac ttgccatgtt atatatatgt agttggcatt    2400
tggttcccaa aaagtaggat gtaggtattt attgtgttct agaaattccg actcttttca    2460
ttagatatat gctatttctt tcattcttgc tggtttatac ctatgttcat ttatatgctg    2520
taaaaaagta gtagcttctt ctacaatgta aaaataaatg tacatacaaa aaaatgcagt    2580
agtatataca atcttttgtt ttgcttcctt tgatagttaa taaattccgt ttgttgaatc    2640
aataaaatac ggcgagccat atgatttgct tcatgagaaa ccagatcaca aacccaaagg    2700
cttaaaacag atagacatta aaatggatat tggccatacc ttcccagcat aatgatgaat    2760
gatgaagcct tggttccaac tgttgaagtg ctcatgactc ccaatctgca tctgaagttt    2820
ctggagcagc gtctgatctg cccctcacc caccgcatgc atcgtggcgc acacgtcatc     2880
caggatgctc atgatgccag gagggttctg atgggagcaa gaaggcaagg ccctagtcac    2940
tgacctctcc aaaacagaca atgcttatca ggtcctttct taggcaagga aacagctccc    3000
cagacttaag ataccatctt gaaagtcagt attccccttc aggcaagaat gcaattaata    3060
gtcccaaata gggagtcacc acttagatct aaagagggag gaaactccac tttccaaaaa   3120
gctgtttaac tccctgaagt ttta                                           3144
```

<210> SEQ ID NO 4
<211> LENGTH: 331
<212> TYPE: PRT
<213> ORGANISM: Mus musculus

<400> SEQUENCE: 4

```
Met Ala Thr Leu Lys Asp Gln Leu Ile Val Asn Leu Leu Lys Glu Glu
 1               5                  10                  15

Gln Ala Pro Gln Asn Lys Ile Thr Val Val Gly Val Gly Ala Val Gly
            20                  25                  30

Met Ala Cys Ala Ile Ser Ile Leu Met Lys Asp Leu Ala Asp Glu Leu
        35                  40                  45

Ala Leu Val Asp Val Met Glu Asp Lys Leu Lys Gly Glu Met Met Asp
    50                  55                  60

Leu Gln His Gly Ser Leu Phe Leu Lys Thr Pro Lys Ile Val Ser Ser
65                  70                  75                  80

Lys Asp Tyr Cys Val Thr Ala Asn Ser Lys Leu Val Ile Ile Thr Ala
                85                  90                  95

Gly Ala Arg Gln Gln Glu Gly Glu Ser Arg Leu Asn Leu Val Gln Arg
            100                 105                 110

Asn Val Asn Ile Phe Lys Phe Ile Ile Pro Asn Ile Val Lys Tyr Ser
```

-continued

```
            115                 120                 125
Pro His Cys Lys Leu Leu Ile Val Ser Asn Pro Val Asp Ile Leu Thr
        130                 135                 140

Tyr Val Ala Trp Lys Ile Ser Gly Phe Pro Lys Asn Arg Val Ile Gly
145                 150                 155                 160

Ser Gly Cys Asn Leu Asp Ser Ala Arg Phe Arg Tyr Leu Met Gly Glu
                165                 170                 175

Arg Leu Gly Val His Ala Leu Ser Cys His Gly Trp Val Leu Gly Glu
                180                 185                 190

His Gly Asp Ser Ser Val Pro Val Trp Ser Gly Val Asn Val Ala Gly
            195                 200                 205

Val Ser Leu Lys Ser Leu Asn Pro Glu Leu Gly Thr Asp Ala Asp Lys
        210                 215                 220

Glu Gln Trp Lys Glu Val His Lys Gln Val Val Asp Ser Ala Tyr Glu
225                 230                 235                 240

Val Ile Lys Leu Lys Gly Tyr Thr Ser Trp Ala Ile Gly Leu Ser Val
                245                 250                 255

Ala Asp Leu Ala Glu Ser Ile Met Lys Asn Leu Arg Arg Val His Pro
            260                 265                 270

Ile Ser Thr Met Ile Lys Gly Leu Tyr Gly Ile Asn Glu Asp Val Phe
        275                 280                 285

Leu Ser Val Pro Cys Ile Leu Gly Gln Asn Gly Ile Ser Asp Val Val
        290                 295                 300

Lys Val Thr Leu Thr Pro Glu Glu Glu Ala Arg Leu Lys Lys Ser Ala
305                 310                 315                 320

Asp Thr Leu Trp Gly Ile Gln Lys Glu Leu Gln
                325                 330
```

ISOLATED HUMAN LACTATE DEHYDROGENASE PROTEINS

RELATED APPLICATIONS

The present application is a divisional of U.S. application Ser. No. 09/711,681, filed on Nov. 9, 2000 and issued on Jan. 7, 2003 as U.S. Pat. No. 6,503,743, which claims benefit of U.S. Provisional Application No. 60/243,477, filed on Oct. 27, 2000 now abandoned.

FIELD OF THE INVENTION

The present invention is in the field of secreted proteins that are related to the lactate dehydrogenase secreted protein subfamily, recombinant DNA molecules, and protein production. The present invention specifically provides novel peptides and proteins that effect protein phosphorylation and nucleic acid molecules encoding such peptide and protein molecules, all of which are useful in the development of human therapeutics and diagnostic compositions and methods.

BACKGROUND OF THE INVENTION

Secreted Proteins

Many human proteins serve as pharmaceutically active compounds. Several classes of human proteins that serve as such active compounds include hormones, cytokines, cell growth factors, and cell differentiation factors. Most proteins that can be used as a pharmaceutically active compound fall within the family of secreted proteins. It is, therefore, important in developing new pharmaceutical compounds to identify secreted proteins that can be tested for activity in a variety of animal models. The present invention advances the state of the art by providing many novel human secreted proteins.

Secreted proteins are generally produced within cells at rough endoplasmic reticulum, are then exported to the golgi complex, and then move to secretory vesicles or granules, where they are secreted to the exterior of the cell via exocytosis.

Secreted proteins are particularly useful as diagnostic markers. Many secreted proteins are found, and can easily be measured, in serum. For example, a 'signal sequence trap' technique can often be utilized because many secreted proteins, such as certain secretory breast cancer proteins, contain a molecular signal sequence for cellular export. Additionally, antibodies against particular secreted serum proteins can serve as potential diagnostic agents, such as for diagnosing cancer.

Secreted proteins play a critical role in a wide array of important biological processes in humans and have numerous utilities; several illustrative examples are discussed herein. For example, fibroblast secreted proteins participate in extracellular matrix formation. Extracellular matrix affects growth factor action, cell adhesion, and cell growth. Structural and quantitative characteristics of fibroblast secreted proteins are modified during the course of cellular aging and such aging related modifications may lead to increased inhibition of cell adhesion, inhibited cell stimulation by growth factors, and inhibited cell proliferative ability (Eleftheriou et al., *Mutat Res* 1991 Mar–Nov;256(2–6): 127–38).

The secreted form of amyloid beta/A4 protein precursor (APP) functions as a growth and/or differentiation factor. The secreted form of APP can stimulate neurite extension of cultured neuroblastoma cells, presumably through binding to a cell surface receptor and thereby triggering intracellular transduction mechanisms. (Roch et al., *Ann N Y Acad Sci* 1993 Sep 24;695:149–57). Secreted APPs modulate neuronal excitability, counteract effects of glutamate on growth cone behaviors, and increase synaptic complexity. The prominent effects of secreted APPs on synaptogenesis and neuronal survival suggest that secreted APPs play a major role in the process of natural cell death and, furthermore, may play a role in the development of a wide variety of neurological disorders, such as stroke, epilepsy, and Alzheimer's disease (Mattson et al., *Perspect Dev Neurobiol* 1998; 5(4):337–52).

Breast cancer cells secrete a 52K estrogen-regulated protein (see Rochefort et al., *Ann N Y Acad Sci* 1986;464:190–201). This secreted protein is therefore useful in breast cancer diagnosis.

Two secreted proteins released by platelets, platelet factor 4 (PF4) and beta-thromboglobulin (betaTG), are accurate indicators of platelet involvement in hemostasis and thrombosis and assays that measure these secreted proteins are useful for studying the pathogenesis and course of thromboembolic disorders (Kaplan, *Adv Exp Med Biol* 1978;102:105–19).

Vascular endothelial growth factor (VEGF) is another example of a naturally secreted protein. VEGF binds to cell-surface heparan sulfates, is generated by hypoxic endothelial cells, reduces apoptosis, and binds to high-affinity receptors that are up-regulated by hypoxia (Asahara et al., *Semin Interv Cardiol* 1996 Sep;1(3):225–32).

Many critical components of the immune system are secreted proteins, such as antibodies, and many important functions of the immune system are dependent upon the action of secreted proteins. For example, Saxon et al., *Biochem Soc Trans* 1997 May;25(2):383–7, discusses secreted IgE proteins.

For a further review of secreted proteins, see Nilsen-Hamilton et al., *Cell Biol Int Rep* 1982 Sep;6(9):815–36.

Lactate Dehydrogenase

Lactate dehydrogenase (LDH), sometimes referred to as lactic dehydrogenase, is the most clinically important dehydrogenase occurring in human serum. LDH is clinically important because serum level of certain isozymes reflect pathological conditions in particular tissues. Consequently, LDH is most often measured to evaluate the presence of tissue damage. LDH serves as an indicator suggestive of disturbances of the cellular integrity induced by pathological conditions. Since LDH is an enzyme present in essentially all major organ systems, serum LDH activity is abnormal in a large number of disorders.

LDH is found in the cytoplasm of cells and catalyzes the following reversible reaction for the interconversion of pyruvate and lactate: Pyruvate+NADH⇌Lactate+AND This bidirectional reaction can be monitored spectrophotometrically by measuring either the increase in NADH at 340 nm produced in the lactate-to-pyruvate reaction, or by measuring the decrease in NADH at 340 nm produced in the pyruvate-to-lactate reaction.

Mammalian LDH exists as five tetrameric isozymes composed of combinations of two different polypeptide subunits with a molecular weight of 136,700±2,100 daltons per tetramer. These tetrameric isozymes each differ in catalytic, physical, and immunological properties. Cahn et al., (1962) designated the two polypeptide subunits as H (heart) and M (muscle), which combine to form two pure types of isozymes, H4 and M4, and three hybrids, H3M, H2M2 and HM3. Type H4 is the most negatively charged at pH 7 and appears nearest the anode upon zone electrophoresis. Subunit H predominates in heart muscle and facilitates the aerobic oxidation of pyruvate. The M subunit predominates in skeletal muscle and liver and is predominantly involved with anaerobic metabolism and pyruvate reduction.

Iodide inhibits LDH; p-mercuribenzoate also inhibits LDH, but at a slower rate. LDH is activated by a number of organic compounds that stabilize the enzyme, such as dimethyl sulfoxide, ethanol, and methanol. Diethystilbestrol and several of its derivatives also stabilize the enzyme.

Normal total LDH levels are approximately 105 to 333 IU/L (international units per liter). Higher than normal LDH levels may be indicative of such conditions as cerebrovascular accident (e.g., CVA, stroke), myocardial infarction, hemolytic anemia (as well as other forms of anemia), hypotension, infectious mononucleosis, intestinal ischemia and infarction, liver disease (e.g., hepatitis), muscle injury, muscular dystrophy, neoplastic conditions, pancreatitis, and pulmonary infarction. If the total LDH level is elevated, specific serum LDH isoenzymes may be measured to increase the accuracy of diagnosis.

The most frequent use of LDH isoenzyme analysis is for the diagnosis of myocardial infarction and other myocardial diseases. Serum LDH levels are elevated in various myocardial diseases and a certain pattern of LDH isoenzyme elevation occurs in myocardial disease. In the absence of hemolysis, an LDH-1/LDH-2 ratio greater than 1 (referred to as a "flipped" ratio) is usually indicative of acute myocardial infarction (AMI). This flipped ratio is observed in about 80% of AMI patients. The normal ratio rarely exceeds 0.80 in the absence of AMI. LDH activity begins to rise 8–12 hrs after the onset of chest pain, peaking at 24–48 hrs, and elevated levels may persist for 1 week or more.

LDH activity and its isoenzyme pattern are also useful indicators of pathological conditions in the lungs, such as cell damage or inflammation. Measurement of LDH activity levels and its isoenzyme pattern in pleural effusion and in bronchoalveolar lavage fluid may provide substantial information about lung and pulmonary endothelial cell injury.

LDH isoenzymes are also useful for evaluating other physiological conditions and disorders such as muscle trauma, liver damage, and a variety of malignancies. In these cases, variations of isoenzyme distribution are useful diagnostic indicators. Serum LDH levels are also useful for diagnosing ovarian dysgerminoma and testicular germ cell tumors. Furthermore, LDH is also useful for establishing the survival duration and rate in Hodgkin's disease and non-Hodgkin's lymphoma, and in the follow-up of ovarian dysgerminoma. Additionally, LDH is also useful for a variety of AND, NADH, NADP and NADPH related studies.

For a further review of lactate dehydrogenases, see: Li, *Prog Clin Biol Res* 1990;344:75–99; Markert et al., *Cell Biochem Funct* 1984 Jul;2(3):131–4; Huijgen et al., *Eur J Clin Chem Clin Biochem* 1997 Aug;35(8):569–79; Drent et al., *Eur Respir J* 1996 Aug;9(8):1736–42; Vanderlinde, *Ann Clin Lab Sci* 1985 Jan–Feb;15(1):13–31; and Wolf, *Clin Lab Med* 1989 Dec;9(4):655–65.

Secreted proteins, particularly members of the lactate dehydrogenase secreted protein subfamily, are a major target for drug action and development. Accordingly, it is valuable to the field of pharmaceutical development to identify and characterize previously unknown members of this subfamily of secreted proteins. The present invention advances the state of the art by providing previously unidentified human secreted proteins that have homology to members of the lactate dehydrogenase secreted protein subfamily.

SUMMARY OF THE INVENTION

The present invention is based in part on the identification of amino acid sequences of human secreted peptides and proteins that are related to the lactate dehydrogenase secreted protein subfamily, as well as allelic variants and other mammalian orthologs thereof. These unique peptide sequences, and nucleic acid sequences that encode these peptides, can be used as models for the development of human therapeutic targets, aid in the identification of therapeutic proteins, and serve as targets for the development of human therapeutic agents that modulate secreted protein activity in cells and tissues that express the secreted protein.

DESCRIPTION OF THE FIGURE SHEETS

FIG. 1A provides the nucleotide sequence of a cDNA molecule or transcript sequence that encodes the secreted protein of the present invention. (SEQ ID NO:1) In addition, structure and functional information is provided, such as ATG start, stop and tissue distribution, where available, that allows one to readily determine specific uses of inventions based on this molecular sequence.

FIGS. 2A and 2B provide the predicted amino acid sequence of the secreted protein of the present invention. (SEQ ID NO:2) In addition structure and functional information such as protein family, function, and modification sites is provided where available, allowing one to readily determine specific uses of inventions based on this molecular sequence.

FIGS. 3A and 3B provide genomic sequences that span the gene encoding the secreted protein of the present invention. (SEQ ID NO:3) In addition structure and functional information, such as intron/exon structure, promoter location, etc., is provided where available, allowing one to readily determine specific uses of inventions based on this molecular sequence. As indicated by the data presented in FIGS. 3A and 3B, the map position was determined to be on chromosome 15.

DETAILED DESCRIPTION OF THE INVENTION

General Description

The present invention is based on the sequencing of the human genome. During the sequencing and assembly of the human genome, analysis of the sequence information revealed previously unidentified fragments of the human genome that encode peptides that share structural and/or sequence homology to protein/peptide/domains identified and characterized within the art as being a secreted protein or part of a secreted protein and are related to the lactate dehydrogenase secreted protein subfamily. Utilizing these sequences, additional genomic sequences were assembled and transcript and/or cDNA sequences were isolated and characterized. Based on this analysis, the present invention provides amino acid sequences of human secreted peptides and proteins that are related to the lactate dehydrogenase secreted protein subfamily, nucleic acid sequences in the form of transcript sequences, cDNA sequences and/or genomic sequences that encode these secreted peptides and proteins, nucleic acid variation (allelic information), tissue distribution of expression, and information about the closest art known protein/peptide/domain that has structural or sequence homology to the secreted protein of the present invention.

In addition to being previously unknown, the peptides that are provided in the present invention are selected based on their ability to be used for the development of commercially important products and services. Specifically, the present peptides are selected based on homology and/or structural relatedness to known secreted proteins of the lactate dehydrogenase secreted protein subfamily and the expression pattern observed. The art has clearly established the commercial importance of members of this family of proteins and proteins that have expression patterns similar to that of the present gene. Some of the more specific features of the peptides of the present invention, and the uses thereof, are described herein, particularly in the Background of the Invention and in the annotation provided in the Figures, and/or are known within the art for each of the known lactate dehydrogenase family or subfamily of secreted proteins.

Specific Embodiments

Peptide Molecules

The present invention provides nucleic acid sequences that encode protein molecules that have been identified as being members of the secreted protein family of proteins and are related to the lactate dehydrogenase secreted protein subfamily (protein sequences are provided in FIGS. 2A and 2B, transcript/cDNA sequences are provided in FIG. 1A and genomic sequences are provided in FIGS. 3A and 3B). The peptide sequences provided in FIGS. 2A and 2B, as well as the obvious variants described herein, particularly allelic variants as identified herein and using the information in FIGS. 3A and 3B, will be referred herein as the secreted peptides of the present invention, secreted peptides, or peptides/proteins of the present invention.

The present invention provides isolated peptide and protein molecules that consist of, consist essentially of, or comprise the amino acid sequences of the secreted peptides, disclosed in the FIGS. 2A and 2B, (encoded by the nucleic acid molecule shown in FIG. 1A, transcript/cDNA or FIG. 3, genomic sequence), as well as all obvious variants of these peptides that are within the art to make and use. Some of these variants are described in detail below.

As used herein, a peptide is said to be "isolated" or "purified" when it is substantially free of cellular material or free of chemical precursors or other chemicals. The peptides of the present invention can be purified to homogeneity or other degrees of purity. The level of purification will be based on the intended use. The critical feature is that the preparation allows for the desired function of the peptide, even if in the presence of considerable amounts of other components (the features of an isolated nucleic acid molecule is discussed below).

In some uses, "substantially free of cellular material" includes preparations of the peptide having less than about 30% (by dry weight) other proteins (i.e., contaminating protein), less than about 20% other proteins, less than about 10% other proteins, or less than about 5% other proteins. When the peptide is recombinantly produced, it can also be substantially free of culture medium, i.e., culture medium represents less than about 20% of the volume of the protein preparation.

The language "substantially free of chemical precursors or other chemicals" includes preparations of the peptide in which it is separated from chemical precursors or other chemicals that are involved in its synthesis. In one embodiment, the language "substantially free of chemical precursors or other chemicals" includes preparations of the secreted peptide having less than about 30% (by dry weight) chemical precursors or other chemicals, less than about 20% chemical precursors or other chemicals, less than about 10% chemical precursors or other chemicals, or less than about 5% chemical precursors or other chemicals.

The isolated secreted peptide can be purified from cells that naturally express it, purified from cells that have been altered to express it (recombinant), or synthesized using known protein synthesis methods. For example, a nucleic acid molecule encoding the secreted peptide is cloned into an expression vector, the expression vector introduced into a host cell and the protein expressed in the host cell. The protein can then be isolated from the cells by an appropriate purification scheme using standard protein purification techniques. Many of these techniques are described in detail below.

Accordingly, the present invention provides proteins that consist of the amino acid sequences provided in FIGS. 2A and 2B (SEQ ID NO:2), for example, proteins encoded by the transcript/cDNA nucleic acid sequences shown in FIG. 1A (SEQ ID NO:1) and the genomic sequences provided in FIGS. 3A and 3B (SEQ ID NO:3). The amino acid sequence of such a protein is provided in FIG. 2. A protein consists of an amino acid sequence when the amino acid sequence is the final amino acid sequence of the protein.

The present invention further provides proteins that consist essentially of the amino acid sequences provided in FIGS. 2A and 2B (SEQ ID NO:2), for example, proteins encoded by the transcript/cDNA nucleic acid sequences shown in FIG. 1A (SEQ ID NO:1) and the genomic sequences provided in FIGS. 3A and 3B (SEQ ID NO:3). A protein consists essentially of an amino acid sequence when such an amino acid sequence is present with only a few additional amino acid residues, for example from about 1 to about 100 or so additional residues, typically from 1 to about 20 additional residues in the final protein.

The present invention further provides proteins that comprise the amino acid sequences provided in FIGS. 2A and 2B (SEQ ID NO:2), for example, proteins encoded by the transcript/cDNA nucleic acid sequences shown in FIG. 1A (SEQ ID NO:1) and the genomic sequences provided in FIGS. 3A and 3B (SEQ ID NO:3). A protein comprises an amino acid sequence when the amino acid sequence is at least part of the final amino acid sequence of the protein. In such a fashion, the protein can be only the peptide or have additional amino acid molecules, such as amino acid residues (contiguous encoded sequence) that are naturally associated with it or heterologous amino acid residues/peptide sequences. Such a protein can have a few additional amino acid residues or can comprise several hundred or more additional amino acids. The preferred classes of proteins that are comprised of the secreted peptides of the present invention are the naturally occurring mature proteins. A brief description of how various types of these proteins can be made/isolated is provided below.

The secreted peptides of the present invention can be attached to heterologous sequences to form chimeric or fusion proteins. Such chimeric and fusion proteins comprise a secreted peptide operatively linked to a heterologous protein having an amino acid sequence not substantially homologous to the secreted peptide. "Operatively linked" indicates that the secreted peptide and the heterologous protein are fused in-frame. The heterologous protein can be fused to the N-terminus or C-terminus of the secreted peptide.

In some uses, the fusion protein does not affect the activity of the secreted peptide per se. For example, the fusion protein can include, but is not limited to, enzymatic fusion proteins, for example beta-galactosidase fusions, yeast two-hybrid GAL fusions, poly-His fusions, MYC-tagged, HI-tagged and Ig fusions. Such fusion proteins, particularly poly-His fusions, can facilitate the purification of recombinant secreted peptide. In certain host cells (e.g., mammalian host cells), expression and/or secretion of a protein can be increased by using a heterologous signal sequence.

A chimeric or fusion protein can be produced by standard recombinant DNA techniques. For example, DNA fragments coding for the different protein sequences are ligated together in-frame in accordance with conventional techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see Ausubel et al., *Current Protocols in Molecular Biology,* 1992). Moreover, many expression vectors are commercially available that already encode a fusion moiety (e.g., a GST protein). A secreted peptide-encoding nucleic acid can be cloned into such an expression vector such that the fusion moiety is linked in-frame to the secreted peptide.

As mentioned above, the present invention also provides and enables obvious variants of the amino acid sequence of the proteins of the present invention, such as naturally occurring mature forms of the peptide, allelic/sequence variants of the peptides, non-naturally occurring recombinantly derived variants of the peptides, and orthologs and paralogs of the peptides. Such variants can readily be generated using art-known techniques in the fields of recombinant nucleic acid technology and protein biochemistry. It is understood, however, that variants exclude any amino acid sequences disclosed prior to the invention.

Such variants can readily be identified/made using molecular techniques and the sequence information disclosed herein. Further, such variants can readily be distinguished from other peptides based on sequence and/or structural homology to the secreted peptides of the present invention. The degree of homology/identity present will be based primarily on whether the peptide is a functional variant or non-functional variant, the amount of divergence present in the paralog family and the evolutionary distance between the orthologs.

To determine the percent identity of two amino acid sequences or two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, at least 30%, 40%, 50%, 60%, 70%, 80%, or 90% or more of the length of a reference sequence is aligned for comparison purposes. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity and similarity between two sequences can be accomplished using a mathematical algorithm. (*Computational Molecular Biology,* Lesk, A. M., ed., Oxford University Press, New York, 1988; *Biocomputing: Informatics and Genome Projects,* Smith, D. W., ed., Academic Press, New York, 1993; *Computer Analysis of Sequence Data,* Part 1, Griffin, A. M., and Griffin, H. G., eds., Humana Press, New Jersey, 1994; *Sequence Analysis in Molecular Biology,* von Heinje, G., Academic Press, 1987; and *Sequence Analysis Primer,* Gribskov, M. and Devereux, J., eds., M Stockton Press, New York, 1991). In a preferred embodiment, the percent identity between two amino acid sequences is determined using the Needleman and Wunsch (*J. Mol. Biol.* (48):444–453 (1970)) algorithm which has been incorporated into the GAP program in the GCG software package, using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (Devereux, J., et al., *Nucleic Acids Res.* 12(1):387 (1984)), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Myers and W. Miller (*CABIOS,* 4:11–17 (1989)) which has been incorporated into the ALIGN program (version 2.0), using a PAM120 weight residue table, a gap length penalty of 12 and a gap penalty of 4.

The nucleic acid and protein sequences of the present invention can further be used as a "query sequence" to perform a search against sequence databases to, for example, identify other family members or related sequences. Such searches can be performed using the NBLAST and XBLAST programs (version 2.0) of Altschul, et al. (*J. Mol. Biol.* 215:403–10 (1990)). BLAST nucleotide searches can be performed with the NBLAST program, score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the proteins of the invention. To obtain gapped alignments for comparison purposes, Gapped BLAST can be utilized as described in Altschul et al. (*Nucleic Acids Res.* 25(17):3389–3402 (1997)). When utilizing BLAST and gapped BLAST programs, the default parameters of the respective programs (e.g., XBLAST and NBLAST) can be used.

Full-length pre-processed forms, as well as mature processed forms, of proteins that comprise one of the peptides of the present invention can readily be identified as having complete sequence identity to one of the secreted peptides of the present invention as well as being encoded by the same genetic locus as the secreted peptide provided herein.

Allelic variants of a secreted peptide can readily be identified as being a human protein having a high degree (significant) of sequence homology/identity to at least a portion of the secreted peptide as well as being encoded by the same genetic locus as the secreted peptide provided herein. Genetic locus can readily be determined based on the genomic information provided in FIG. 3, such as the genomic sequence mapped to the reference human. As indicated by the data presented in FIG. 3, the map position was determined to be on chromosome 15. As used herein, two proteins (or a region of the proteins) have significant homology when the amino acid sequences are typically at least about 70–80%, 80–90%, and more typically at least about 90–95% or more homologous. A significantly homologous amino acid sequence, according to the present invention, will be encoded by a nucleic acid sequence that will hybridize to a secreted peptide encoding nucleic acid molecule under stringent conditions as more fully described below.

Paralogs of a secreted peptide can readily be identified as having some degree of significant sequence homology/identity to at least a portion of the secreted peptide, as being encoded by a gene from humans, and as having similar activity or function. Two proteins will typically be considered paralogs when the amino acid sequences are typically at least about 60% or greater, and more typically at least about 70% or greater homology through a given region or domain. Such paralogs will be encoded by a nucleic acid sequence that will hybridize to a secreted peptide encoding nucleic acid molecule under moderate to stringent conditions as more fully described below.

Orthologs of a secreted peptide can readily be identified as having some degree of significant sequence homology/identity to at least a portion of the secreted peptide as well as being encoded by a gene from another organism. Preferred orthologs will be isolated from mammals, preferably primates, for the development of human therapeutic targets and agents. Such orthologs will be encoded by a nucleic acid sequence that will hybridize to a secreted peptide encoding nucleic acid molecule under moderate to stringent conditions, as more fully described below, depending on the degree of relatedness of the two organisms yielding the proteins.

Non-naturally occurring variants of the secreted peptides of the present invention can readily be generated using recombinant techniques. Such variants include, but are not limited to deletions, additions and substitutions in the amino acid sequence of the secreted peptide. For example, one class of substitutions are conserved amino acid substitution. Such substitutions are those that substitute a given amino acid in a secreted peptide by another amino acid of like characteristics. Typically seen as conservative substitutions are the replacements, one for another, among the aliphatic amino acids Ala, Val, Leu, and Ile; interchange of the hydroxyl residues Ser and Thr; exchange of the acidic residues Asp and Glu; substitution between the amide residues Asn and Gln; exchange of the basic residues Lys and Arg; and replacements among the aromatic residues Phe and Tyr. Guidance concerning which amino acid changes are likely to be phenotypically silent are found in Bowie et al., *Science* 247:1306–1310 (1990).

Variant secreted peptides can be fully functional or can lack function in one or more activities, e.g. ability to bind substrate, ability to phosphorylate substrate, ability to mediate signaling, etc. Fully functional variants typically contain only conservative variation or variation in non-critical residues or in non-critical regions. FIG. 2 provides the result of protein analysis and can be used to identify critical domains/regions. Functional variants can also contain substitution of similar amino acids that result in no change or an insignificant change in function. Alternatively, such substitutions may positively or negatively affect function to some degree.

Non-functional variants typically contain one or more non-conservative amino acid substitutions, deletions, insertions, inversions, or truncation or a substitution, insertion, inversion, or deletion in a critical residue or critical region.

Amino acids that are essential for function can be identified by methods known in the art, such as site-directed mutagenesis or alanine-scanning mutagenesis (Cunningham et al., *Science* 244:1081–1085 (1989)), particularly using the results provided in FIG. 2. The latter procedure introduces single alanine mutations at every residue in the molecule. The resulting mutant molecules are then tested for biological activity such as secreted protein activity or in assays such as an in vitro proliferative activity. Sites that are critical for binding partner/substrate binding can also be determined by structural analysis such as crystallization, nuclear magnetic resonance or photoaffinity labeling (Smith et al., *J. Mol. Biol.* 224:899–904 (1992); de Vos et al. *Science* 255:306–312 (1992)).

The present invention further provides fragments of the secreted peptides, in addition to proteins and peptides that comprise and consist of such fragments, particularly those comprising the residues identified in FIG. 2. The fragments to which the invention pertains, however, are not to be construed as encompassing fragments that may be disclosed publicly prior to the present invention.

As used herein, a fragment comprises at least 8, 10, 12, 14, 16, or more contiguous amino acid residues from a secreted peptide. Such fragments can be chosen based on the ability to retain one or more of the biological activities of the secreted peptide or could be chosen for the ability to perform a function, e.g. bind a substrate or act as an immunogen. Particularly important fragments are biologically active fragments, peptides that are, for example, about 8 or more amino acids in length. Such fragments will typically comprise a domain or motif of the secreted peptide, e.g., active site or a substrate-binding domain. Further, possible fragments include, but are not limited to, domain or motif containing fragments, soluble peptide fragments, and fragments containing immunogenic structures. Predicted domains and functional sites are readily identifiable by computer programs well known and readily available to those of skill in the art (e.g., PROSITE analysis). The results of one such analysis are provided in FIG. 2.

Polypeptides often contain amino acids other than the 20 amino acids commonly referred to as the 20 naturally occurring amino acids. Further, many amino acids, including the terminal amino acids, may be modified by natural processes, such as processing and other post-translational modifications, or by chemical modification techniques well known in the art. Common modifications that occur naturally in secreted peptides are described in basic texts, detailed monographs, and the research literature, and they are well known to those of skill in the art (some of these features are identified in FIG. 2).

Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well known to those of skill in the art and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as *Proteins—Structure and Molecular Properties*, 2nd Ed., T. E. Creighton, W. H. Freeman and Company, New York (1993). Many detailed reviews are available on this subject, such as by Wold, F., *Posttranslational Covalent Modification of Proteins*, B. C. Johnson, Ed., Academic Press, New York 1–12 (1983); Seifter et al (*Meth. Enzymol.* 182: 626–646 (1990)) and Rattan et al (*Ann. N. Y. Acad. Sci.* 663:48–62 (1992)).

Accordingly, the secreted peptides of the present invention also encompass derivatives or analogs in which a substituted amino acid residue is not one encoded by the genetic code, in which a substituent group is included, in which the mature secreted peptide is fused with another compound, such as a compound to increase the half-life of the secreted peptide (for example, polyethylene glycol), or in which the additional amino acids are fused to the mature secreted peptide, such as a leader or secretory sequence or a sequence for purification of the mature secreted peptide or a pro-protein sequence.

Protein/Peptide Uses

The proteins of the present invention can be used in substantial and specific assays related to the functional information provided in the Figures; to raise antibodies or to elicit another immune response; as a reagent (including the labeled reagent) in assays designed to quantitatively determine levels of the protein (or its binding partner or ligand) in biological fluids; and as markers for tissues in which the corresponding protein is preferentially expressed (either constitutively or at a particular stage of tissue differentiation or development or in a disease state). Where the protein binds or potentially binds to another protein or ligand (such as, for example, in a secreted protein-effector protein interaction or secreted protein-ligand interaction), the protein can be used to identify the binding partner/ligand so as to develop a system to identify inhibitors of the binding interaction. Any or all of these uses are capable of being developed into reagent grade or kit format for commercialization as commercial products.

Methods for performing the uses listed above are well known to those skilled in the art. References disclosing such methods include "Molecular Cloning: A Laboratory Manual", 2d ed., Cold Spring Harbor Laboratory Press, Sambrook, J., E. F. Fritsch and T. Maniatis eds., 1989, and "Methods in Enzymology: Guide to Molecular Cloning Techniques", Academic Press, Berger, S. L. and A. R. Kimmel eds., 1987.

The potential uses of the peptides of the present invention are based primarily on the source of the protein as well as the class/action of the protein. For example, secreted proteins isolated from humans and their human/mammalian orthologs serve as targets for identifying agents for use in mammalian therapeutic applications, e.g. a human drug, particularly in modulating a biological or pathological response in a cell or tissue that expresses the secreted protein. A large percentage of pharmaceutical agents are being developed that modulate the activity of secreted proteins, particularly members of the lactate dehydrogenase subfamily (see Background of the Invention). The structural and functional information provided in the Background and Figures provide specific and substantial uses for the molecules of the present invention, particularly in combination with the expression information provided in FIG. 1. Such uses can readily be determined using the information provided herein, that which is known in the art, and routine experimentation.

The proteins of the present invention (including variants and fragments that may have been disclosed prior to the present invention) are useful for biological assays related to secreted proteins that are related to members of the lactate dehydrogenase subfamily. Such assays involve any of the known secreted protein functions or activities or properties useful for diagnosis and treatment of secreted protein-related conditions that are specific for the subfamily of secreted proteins that the one of the present invention belongs to, particularly in cells and tissues that express the secreted protein.

The proteins of the present invention are also useful in drug screening assays, in cell-based or cell-free systems. Cell-based systems can be native, i.e., cells that normally express the secreted protein, as a biopsy or expanded in cell culture. In an alternate embodiment, cell-based assays involve recombinant host cells expressing the secreted protein.

The polypeptides can be used to identify compounds that modulate secreted protein activity of the protein in its natural state or an altered form that causes a specific disease or pathology associated with the secreted protein. Both the secreted proteins of the present invention and appropriate variants and fragments can be used in high-throughput screens to assay candidate compounds for the ability to bind to the secreted protein. These compounds can be further screened against a functional secreted protein to determine the effect of the compound on the secreted protein activity. Further, these compounds can be tested in animal or invertebrate systems to determine activity/effectiveness. Compounds can be identified that activate (agonist) or inactivate (antagonist) the secreted protein to a desired degree.

Further, the proteins of the present invention can be used to screen a compound for the ability to stimulate or inhibit interaction between the secreted protein and a molecule that normally interacts with the secreted protein, e.g. a substrate or a component of the signal pathway that the secreted protein normally interacts (for example, another secreted protein). Such assays typically include the steps of combining the secreted protein with a candidate compound under conditions that allow the secreted protein, or fragment, to interact with the target molecule, and to detect the formation of a complex between the protein and the target or to detect the biochemical consequence of the interaction with the secreted protein and the target.

Candidate compounds include, for example, 1) peptides such as soluble peptides, including Ig-tailed fusion peptides and members of random peptide libraries (see, e.g., Lam et al., *Nature* 354:82–84 (1991); Houghten et al., *Nature* 354:84–86 (1991)) and combinatorial chemistry-derived molecular libraries made of D- and/or L-configuration amino acids; 2) phosphopeptides (e.g., members of random and partially degenerate, directed phosphopeptide libraries, see, e.g., Songyang et al., *Cell* 72:767–778 (1993)); 3) antibodies (e.g., polyclonal, monoclonal, humanized, anti-idiotypic, chimeric, and single chain antibodies as well as Fab, F(ab')$_2$, Fab expression library fragments, and epitope-binding fragments of antibodies); and 4) small organic and inorganic molecules (e.g., molecules obtained from combinatorial and natural product libraries).

One candidate compound is a soluble fragment of the receptor that competes for substrate binding. Other candidate compounds include mutant secreted proteins or appropriate fragments containing mutations that affect secreted protein function and thus compete for substrate. Accordingly, a fragment that competes for substrate, for example with a higher affinity, or a fragment that binds substrate but does not allow release, is encompassed by the invention.

Any of the biological or biochemical functions mediated by the secreted protein can be used as an endpoint assay. These include all of the biochemical or biochemical/biological events described herein, in the references cited herein, incorporated by reference for these endpoint assay targets, and other functions known to those of ordinary skill in the art or that can be readily identified using the information provided in the Figures, particularly FIG. 2. Specifically, a biological function of a cell or tissues that expresses the secreted protein can be assayed.

Binding and/or activating compounds can also be screened by using chimeric secreted proteins in which the amino terminal extracellular domain, or parts thereof, the entire transmembrane domain or subregions, such as any of the seven transmembrane segments or any of the intracellular or extracellular loops and the carboxy terminal intracellular domain, or parts thereof, can be replaced by heterologous domains or subregions. For example, a substrate-binding region can be used that interacts with a different substrate then that which is recognized by the native secreted protein. Accordingly, a different set of signal transduction components is available as an end-point assay for activation. This allows for assays to be performed in other than the specific host cell from which the secreted protein is derived.

The proteins of the present invention are also useful in competition binding assays in methods designed to discover compounds that interact with the secreted protein (e.g. binding partners and/or ligands). Thus, a compound is exposed to a secreted protein polypeptide under conditions that allow the compound to bind or to otherwise interact with the polypeptide. Soluble secreted protein polypeptide is also added to the mixture. If the test compound interacts with the soluble secreted protein polypeptide, it decreases the amount of complex formed or activity from the secreted protein target. This type of assay is particularly useful in cases in which compounds are sought that interact with specific regions of the secreted protein. Thus, the soluble polypeptide that competes with the target secreted protein region is designed to contain peptide sequences corresponding to the region of interest.

To perform cell free drug screening assays, it is sometimes desirable to immobilize either the secreted protein, or fragment, or its target molecule to facilitate separation of complexes from uncomplexed forms of one or both of the proteins, as well as to accommodate automation of the assay.

Techniques for immobilizing proteins on matrices can be used in the drug screening assays. In one embodiment, a fusion protein can be provided which adds a domain that allows the protein to be bound to a matrix. For example, glutathione-S-transferase fusion proteins can be adsorbed onto glutathione sepharose beads (Sigma Chemical, St. Louis, Mo.) or glutathione derivatized microtitre plates, which are then combined with the cell lysates (e.g., $^{35}$S-labeled) and the candidate compound, and the mixture incubated under conditions conducive to complex formation (e.g., at physiological conditions for salt and pH). Following incubation, the beads are washed to remove any unbound label, and the matrix immobilized and radiolabel determined directly, or in the supernatant after the complexes are dissociated. Alternatively, the complexes can be dissociated from the matrix, separated by SDS-PAGE, and the level of secreted protein-binding protein found in the bead fraction quantitated from the gel using standard electrophoretic techniques. For example, either the polypeptide or its target molecule can be immobilized utilizing conjugation of biotin and streptavidin using techniques well known in the art. Alternatively, antibodies reactive with the protein but which do not interfere with binding of the protein to its target molecule can be derivatized to the wells of the plate, and the protein trapped in the wells by antibody conjugation. Preparations of a secreted protein-binding protein and a candidate compound are incubated in the secreted protein-presenting wells and the amount of complex trapped in the well can be quantitated. Methods for detecting such complexes, in addition to those described above for the GST-immobilized complexes, include immunodetection of complexes using antibodies reactive with the secreted protein target molecule, or which are reactive with secreted protein and compete with the target molecule, as well as enzyme-linked assays which rely on detecting an enzymatic activity associated with the target molecule.

Agents that modulate one of the secreted proteins of the present invention can be identified using one or more of the above assays, alone or in combination. It is generally preferable to use a cell-based or cell free system first and then confirm activity in an animal or other model system. Such model systems are well known in the art and can readily be employed in this context.

Modulators of secreted protein activity identified according to these drug screening assays can be used to treat a subject with a disorder mediated by the secreted protein pathway, by treating cells or tissues that express the secreted protein. These methods of treatment include the steps of administering a modulator of secreted protein activity in a pharmaceutical composition to a subject in need of such treatment, the modulator being identified as described herein.

In yet another aspect of the invention, the secreted proteins can be used as "bait proteins" in a two-hybrid assay or three-hybrid assay (see, e.g., U.S. Pat. No. 5,283,317; Zervos et al. (1993) Cell 72:223–232; Madura et al. (1993) J. Biol. Chem. 268:12046–12054; Bartel et al. (1993) Biotechniques 14:920–924; Iwabuchi et al. (1993) Oncogene 8:1693–1696; and Brent WO94/10300), to identify other proteins, which bind to or interact with the secreted protein and are involved in secreted protein activity.

The two-hybrid system is based on the modular nature of most transcription factors, which consist of separable DNA-binding and activation domains. Briefly, the assay utilizes two different DNA constructs. In one construct, the gene that codes for a secreted protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a secreted protein-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the secreted protein.

This invention further pertains to novel agents identified by the above-described screening assays. Accordingly, it is within the scope of this invention to further use an agent identified as described herein in an appropriate animal model. For example, an agent identified as described herein (e.g., a secreted protein-modulating agent, an antisense secreted protein nucleic acid molecule, a secreted protein-specific antibody, or a secreted protein-binding partner) can be used in an animal or other model to determine the efficacy, toxicity, or side effects of treatment with such an agent. Alternatively, an agent identified as described herein can be used in an animal or other model to determine the mechanism of action of such an agent. Furthermore, this invention pertains to uses of novel agents identified by the above-described screening assays for treatments as described herein.

The secreted proteins of the present invention are also useful to provide a target for diagnosing a disease or predisposition to disease mediated by the peptide. Accordingly, the invention provides methods for detecting the presence, or levels of, the protein (or encoding mRNA) in a cell, tissue, or organism. The method involves contacting a biological sample with a compound capable of interacting with the secreted protein such that the interaction can be detected. Such an assay can be provided in a single detection format or a multi-detection format such as an antibody chip array.

One agent for detecting a protein in a sample is an antibody capable of selectively binding to protein. A biological sample includes tissues, cells and biological fluids isolated from a subject, as well as tissues, cells and fluids present within a subject.

The peptides of the present invention also provide targets for diagnosing active protein activity, disease, or predisposition to disease, in a patient having a variant peptide, particularly activities and conditions that are known for other members of the family of proteins to which the present one belongs. Thus, the peptide can be isolated from a biological sample and assayed for the presence of a genetic mutation that results in aberrant peptide. This includes amino acid substitution, deletion, insertion, rearrangement, (as the result of aberrant splicing events), and inappropriate post-translational modification. Analytic methods include altered electrophoretic mobility, altered tryptic peptide digest, altered secreted protein activity in cell-based or cell-free assay, alteration in substrate or antibody-binding pattern, altered isoelectric point, direct amino acid sequencing, and any other of the known assay techniques useful for detecting mutations in a protein. Such an assay can be provided in a single detection format or a multi-detection format such as an antibody chip array.

In vitro techniques for detection of peptide include enzyme linked immunosorbent assays (ELISAs), Western blots, immunoprecipitations and immunofluorescence using a detection reagent, such as an antibody or protein binding agent. Alternatively, the peptide can be detected in vivo in a subject by introducing into the subject a labeled anti-peptide antibody or other types of detection agent. For example, the antibody can be labeled with a radioactive marker whose presence and location in a subject can be detected by standard imaging techniques. Particularly useful are methods that detect the allelic variant of a peptide expressed in a subject and methods which detect fragments of a peptide in a sample.

The peptides are also useful in pharmacogenomic analysis. Pharmacogenomics deal with clinically significant hereditary variations in the response to drugs due to altered drug disposition and abnormal action in affected persons. See, e.g., Eichelbaum, M. (Clin. Exp. Pharmacol. Physiol. 23(10–11):983–985 (1996)), and Linder, M. W. (Clin. Chem. 43(2):254–266 (1997)). The clinical outcomes of these variations result in severe toxicity of therapeutic drugs in certain individuals or therapeutic failure of drugs in certain individuals as a result of individual variation in metabolism. Thus, the genotype of the individual can determine the way a therapeutic compound acts on the body or the way the body metabolizes the compound. Further, the activity of drug metabolizing enzymes effects both the intensity and duration of drug action. Thus, the pharmacogenomics of the individual permit the selection of effective compounds and effective dosages of such compounds for prophylactic or therapeutic treatment based on the individual's genotype. The discovery of genetic polymorphisms in some drug metabolizing enzymes has explained why some patients do not obtain the expected drug effects, show an exaggerated drug effect, or experience serious toxicity from standard drug dosages. Polymorphisms can be expressed in the phenotype of the extensive metabolizer and the phenotype of the poor metabolizer. Accordingly, genetic polymorphism may lead to allelic protein variants of the secreted protein in which one or more of the secreted protein functions in one population is different from those in another population. The peptides thus allow a target to ascertain a genetic predisposition that can affect treatment modality. Thus, in a ligand-based treatment, polymorphism may give rise to amino terminal extracellular domains and/or other substrate-binding regions that are more or less active in substrate binding, and secreted protein activation. Accordingly, substrate dosage would necessarily be modified to maximize the therapeutic effect within a given population containing a polymorphism. As an alternative to genotyping, specific polymorphic peptides could be identified.

The peptides are also useful for treating a disorder characterized by an absence of, inappropriate, or unwanted expression of the protein. Accordingly, methods for treatment include the use of the secreted protein or fragments.

Antibodies

The invention also provides antibodies that selectively bind to one of the peptides of the present invention, a protein comprising such a peptide, as well as variants and fragments thereof. As used herein, an antibody selectively binds a target peptide when it binds the target peptide and does not significantly bind to unrelated proteins. An antibody is still considered to selectively bind a peptide even if it also binds to other proteins that are not substantially homologous with the target peptide so long as such proteins share homology with a fragment or domain of the peptide target of the antibody. In this case, it would be understood that antibody binding to the peptide is still selective despite some degree of cross-reactivity.

As used herein, an antibody is defined in terms consistent with that recognized within the art: they are multi-subunit proteins produced by a mammalian organism in response to an antigen challenge. The antibodies of the present invention include polyclonal antibodies and monoclonal antibodies, as well as fragments of such antibodies, including, but not limited to, Fab or F(ab')$_2$, and Fv fragments.

Many methods are known for generating and/or identifying antibodies to a given target peptide. Several such methods are described by Harlow, Antibodies, Cold Spring Harbor Press, (1989).

In general, to generate antibodies, an isolated peptide is used as an immunogen and is administered to a mammalian organism, such as a rat, rabbit or mouse. The full-length protein, an antigenic peptide fragment or a fusion protein can be used. Particularly important fragments are those covering functional domains, such as the domains identified in FIG. 2, and domain of sequence homology or divergence amongst the family, such as those that can readily be identified using protein alignment methods and as presented in the Figures.

Antibodies are preferably prepared from regions or discrete fragments of the secreted proteins. Antibodies can be prepared from any region of the peptide as described herein. However, preferred regions will include those involved in function/activity and/or secreted protein/binding partner interaction. FIG. 2 can be used to identify particularly important regions while sequence alignment can be used to identify conserved and unique sequence fragments.

An antigenic fragment will typically comprise at least 8 contiguous amino acid residues. The antigenic peptide can comprise, however, at least 10, 12, 14, 16 or more amino acid residues. Such fragments can be selected on a physical property, such as fragments correspond to regions that are located on the surface of the protein, e.g., hydrophilic regions or can be selected based on sequence uniqueness (see FIG. 2).

Detection on an antibody of the present invention can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

Antibody Uses

The antibodies can be used to isolate one of the proteins of the present invention by standard techniques, such as affinity chromatography or immunoprecipitation. The antibodies can facilitate the purification of the natural protein from cells and recombinantly produced protein expressed in host cells. In addition, such antibodies are useful to detect the presence of one of the proteins of the present invention in cells or tissues to determine the pattern of expression of the protein among various tissues in an organism and over the course of normal development. Further, such antibodies can be used to detect protein in situ, in vitro, or in a cell lysate or supernatant in order to evaluate the abundance and pattern of expression. Also, such antibodies can be used to assess abnormal tissue distribution or abnormal expression during development or progression of a biological condition. Antibody detection of circulating fragments of the full length protein can be used to identify turnover.

Further, the antibodies can be used to assess expression in disease states such as in active stages of the disease or in an individual with a predisposition toward disease related to the protein's function. When a disorder is caused by an inappropriate tissue distribution, developmental expression, level of expression of the protein, or expressed/processed form, the antibody can be prepared against the normal protein. If a disorder is characterized by a specific mutation in the protein, antibodies specific for this mutant protein can be used to assay for the presence of the specific mutant protein.

The antibodies can also be used to assess normal and aberrant subcellular localization of cells in the various tissues in an organism. The diagnostic uses can be applied, not only in genetic testing, but also in monitoring a treatment modality. Accordingly, where treatment is ultimately aimed at correcting expression level or the presence of aberrant sequence and aberrant tissue distribution or developmental expression, antibodies directed against the protein or relevant fragments can be used to monitor therapeutic efficacy.

Additionally, antibodies are useful in pharmacogenomic analysis. Thus, antibodies prepared against polymorphic proteins can be used to identify individuals that require modified treatment modalities. The antibodies are also useful as diagnostic tools as an immunological marker for aberrant protein analyzed by electrophoretic mobility, isoelectric point, tryptic peptide digest, and other physical assays known to those in the art.

The antibodies are also useful for tissue typing. Thus, where a specific protein has been correlated with expression in a specific tissue, antibodies that are specific for this protein can be used to identify a tissue type.

The antibodies are also useful for inhibiting protein function, for example, blocking the binding of the secreted peptide to a binding partner such as a substrate. These uses can also be applied in a therapeutic context in which treatment involves inhibiting the protein's function. An antibody can be used, for example, to block binding, thus modulating (agonizing or antagonizing) the peptides activity. Antibodies can be prepared against specific fragments containing sites required for function or against intact protein that is associated with a cell or cell membrane. See FIG. 2 for structural information relating to the proteins of the present invention.

The invention also encompasses kits for using antibodies to detect the presence of a protein in a biological sample. The kit can comprise antibodies such as a labeled or labelable antibody and a compound or agent for detecting protein in a biological sample; means for determining the amount of protein in the sample; means for comparing the amount of protein in the sample with a standard; and instructions for use. Such a kit can be supplied to detect a single protein or epitope or can be configured to detect one of a multitude of epitopes, such as in an antibody detection array. Arrays are described in detail below for nuleic acid arrays and similar methods have been developed for antibody arrays.

Nucleic Acid Molecules

The present invention further provides isolated nucleic acid molecules that encode a secreted peptide or protein of the present invention (cDNA, transcript and genomic sequence). Such nucleic acid molecules will consist of, consist essentially of, or comprise a nucleotide sequence that encodes one of the secreted peptides of the present invention, an allelic variant thereof, or an ortholog or paralog thereof.

As used herein, an "isolated" nucleic acid molecule is one that is separated from other nucleic acid present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. However, there can be some flanking nucleotide sequences, for example up to about 5 KB, 4 KB, 3 KB, 2 KB, or 1 KB or less, particularly contiguous peptide encoding sequences and peptide encoding sequences within the same gene but separated by introns in the genomic sequence. The important point is that the nucleic acid is isolated from remote and unimportant flanking sequences such that it can be subjected to the specific manipulations described herein such as recombinant expression, preparation of probes and primers, and other uses specific to the nucleic acid sequences.

Moreover, an "isolated" nucleic acid molecule, such as a transcript/cDNA molecule, can be substantially free of other cellular material, or culture medium when produced by recombinant techniques, or chemical precursors or other chemicals when chemically synthesized. However, the nucleic acid molecule can be fused to other coding or regulatory sequences and still be considered isolated.

For example, recombinant DNA molecules contained in a vector are considered isolated. Further examples of isolated DNA molecules include recombinant DNA molecules maintained in heterologous host cells or purified (partially or substantially) DNA molecules in solution. Isolated RNA molecules include in vivo or in vitro RNA transcripts of the isolated DNA molecules of the present invention. Isolated nucleic acid molecules according to the present invention further include such molecules produced synthetically.

Accordingly, the present invention provides nucleic acid molecules that consist of the nucleotide sequence shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule consists of a nucleotide sequence when the nucleotide sequence is the complete nucleotide sequence of the nucleic acid molecule.

The present invention further provides nucleic acid molecules that consist essentially of the nucleotide sequence shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule consists essentially of a nucleotide sequence when such a nucleotide sequence is present with only a few additional nucleic acid residues in the final nucleic acid molecule.

The present invention further provides nucleic acid molecules that comprise the nucleotide sequences shown in FIG. 1 or 3 (SEQ ID NO: 1, transcript sequence and SEQ ID NO:3, genomic sequence), or any nucleic acid molecule that encodes the protein provided in FIG. 2, SEQ ID NO:2. A nucleic acid molecule comprises a nucleotide sequence when the nucleotide sequence is at least part of the final nucleotide sequence of the nucleic acid molecule. In such a fashion, the nucleic acid molecule can be only the nucleotide sequence or have additional nucleic acid residues, such as nucleic acid residues that are naturally associated with it or heterologous nucleotide sequences. Such a nucleic acid molecule can have a few additional nucleotides or can comprises several hundred or more additional nucleotides. A brief description of how various types of these nucleic acid molecules can be readily made/isolated is provided below.

In FIGS. 1 and 3, both coding and non-coding sequences are provided. Because of the source of the present invention, humans genomic sequence (FIG. 3) and cDNA/transcript sequences (FIG. 1), the nucleic acid molecules in the Figures will contain genomic intronic sequences, 5' and 3' non-coding sequences, gene regulatory regions and non-coding intergenic sequences. In general such sequence features are either noted in FIGS. 1 and 3 or can readily be identified using computational tools known in the art. As discussed below, some of the non-coding regions, particularly gene regulatory elements such as promoters, are useful for a variety of purposes, e.g. control of heterologous gene expression, target for identifying gene activity modulating compounds, and are particularly claimed as fragments of the genomic sequence provided herein.

The isolated nucleic acid molecules can encode the mature protein plus additional amino or carboxyl-terminal amino acids, or amino acids interior to the mature peptide (when the mature form has more than one peptide chain, for instance). Such sequences may play a role in processing of a protein from precursor to a mature form, facilitate protein trafficking, prolong or shorten protein half-life or facilitate manipulation of a protein for assay or production, among other things. As generally is the case in situ, the additional amino acids may be processed away from the mature protein by cellular enzymes.

As mentioned above, the isolated nucleic acid molecules include, but are not limited to, the sequence encoding the secreted peptide alone, the sequence encoding the mature peptide and additional coding sequences, such as a leader or secretory sequence (e.g., a pre- pro or pro-protein sequence), the sequence encoding the mature peptide, with or without the additional coding sequences, plus additional non-coding sequences, for example introns and non-coding 5' and 3' sequences such as transcribed but non-translated sequences that play a role in transcription, mRNA processing (including splicing and polyadenylation signals), ribosome binding and stability of mRNA. In addition, the nucleic acid molecule may be fused to a marker sequence encoding, for example, a peptide that facilitates purification.

Isolated nucleic acid molecules can be in the form of RNA, such as mRNA, or in the form DNA, including cDNA and genomic DNA obtained by cloning or produced by chemical synthetic techniques or by a combination thereof. The nucleic acid, especially DNA, can be double-stranded or single-stranded. Single-stranded nucleic acid can be the coding strand (sense strand) or the non-coding strand (anti-sense strand).

The invention further provides nucleic acid molecules that encode fragments of the peptides of the present invention as well as nucleic acid molecules that encode obvious variants of the secreted proteins of the present invention that are described above. Such nucleic acid molecules may be naturally occurring, such as allelic variants (same locus), paralogs (different locus), and orthologs (different organism), or may be constructed by recombinant DNA methods or by chemical synthesis. Such non-naturally occurring variants may be made by mutagenesis techniques, including those applied to nucleic acid molecules, cells, or organisms. Accordingly, as discussed above, the variants can contain nucleotide substitutions, deletions, inversions and insertions. Variation can occur in either or both the coding and non-coding regions. The variations can produce both conservative and non-conservative amino acid substitutions.

The present invention further provides non-coding fragments of the nucleic acid molecules provided in FIGS. 1 and 3. Preferred non-coding fragments include, but are not limited to, promoter sequences, enhancer sequences, gene modulating sequences and gene termination sequences. Such fragments are useful in controlling heterologous gene expression and in developing screens to identify gene-modulating agents. A promoter can readily be identified as being 5' to the ATG start site in the genomic sequence provided in FIG. 3.

A fragment comprises a contiguous nucleotide sequence greater than 12 or more nucleotides. Further, a fragment could at least 30, 40, 50, 100, 250 or 500 nucleotides in length. The length of the fragment will be based on its intended use. For example, the fragment can encode epitope bearing regions of the peptide, or can be useful as DNA probes and primers. Such fragments can be isolated using the known nucleotide sequence to synthesize an oligonucleotide probe. A labeled probe can then be used to screen a cDNA library, genomic DNA library, or mRNA to isolate nucleic acid corresponding to the coding region. Further, primers can be used in PCR reactions to clone specific regions of gene.

A probe/primer typically comprises substantially a purified oligonucleotide or oligonucleotide pair. The oligonucleotide typically comprises a region of nucleotide sequence that hybridizes under stringent conditions to at least about 12, 20, 25, 40, 50 or more consecutive nucleotides.

Orthologs, homologs, and allelic variants can be identified using methods well known in the art. As described in the Peptide Section, these variants comprise a nucleotide sequence encoding a peptide that is typically 60–70%, 70–80%, 80–90%, and more typically at least about 90–95% or more homologous to the nucleotide sequence shown in the Figure sheets or a fragment of this sequence. Such nucleic acid molecules can readily be identified as being able to hybridize under moderate to stringent conditions, to the nucleotide sequence shown in the Figure sheets or a fragment of the sequence. Allelic variants can readily be determined by genetic locus of the encoding gene.

As used herein, the term "hybridizes under stringent conditions" is intended to describe conditions for hybridization and washing under which nucleotide sequences encoding a peptide at least 60–70% homologous to each other typically remain hybridized to each other. The conditions can be such that sequences at least about 60%, at least about 70%, or at least about 80% or more homologous to each other typically remain hybridized to each other. Such stringent conditions are known to those skilled in the art and can be found in Current Protocols in Molecular Biology, John Wiley & Sons, N.Y. (1989), 6.3.1–6.3.6. One example of stringent hybridization conditions are hybridization in 6×sodium chloride/sodium citrate (SSC) at about 45 C., followed by one or more washes in 0.2×SSC, 0.1% SDS at 50–65 C. Examples of moderate to low stringency hybridization conditions are well known in the art.

Nucleic Acid Molecule Uses

The nucleic acid molecules of the present invention are useful for probes, primers, chemical intermediates, and in biological assays. The nucleic acid molecules are useful as a hybridization probe for messenger RNA, transcript/cDNA and genomic DNA to isolate full-length cDNA and genomic clones encoding the peptide described in FIG. 2 and to isolate cDNA and genomic clones that correspond to variants (alleles, orthologs, etc.) producing the same or related peptides shown in FIG. 2.

The probe can correspond to any sequence along the entire length of the nucleic acid molecules provided in the Figures. Accordingly, it could be derived from 5' noncoding regions, the coding region, and 3' noncoding regions. However, as discussed, fragments are not to be construed as encompassing fragments disclosed prior to the present invention.

The nucleic acid molecules are also useful as primers for PCR to amplify any given region of a nucleic acid molecule and are useful to synthesize antisense molecules of desired length and sequence.

The nucleic acid molecules are also useful for constructing recombinant vectors. Such vectors include expression vectors that express a portion of, or all of, the peptide sequences. Vectors also include insertion vectors, used to integrate into another nucleic acid molecule sequence, such as into the cellular genome, to alter in situ expression of a gene and/or gene product. For example, an endogenous coding sequence can be replaced via homologous recombination with all or part of the coding region containing one or more specifically introduced mutations.

The nucleic acid molecules are also useful for expressing antigenic portions of the proteins.

The nucleic acid molecules are also useful as probes for determining the chromosomal positions of the nucleic acid molecules by means of in situ hybridization methods.

The nucleic acid molecules are also useful in making vectors containing the gene regulatory regions of the nucleic acid molecules of the present invention.

The nucleic acid molecules are also useful for designing ribozymes corresponding to all, or a part, of the mRNA produced from the nucleic acid molecules described herein.

The nucleic acid molecules are also useful for making vectors that express part, or all, of the peptides.

The nucleic acid molecules are also useful for constructing host cells expressing a part, or all, of the nucleic acid molecules and peptides.

The nucleic acid molecules are also useful for constructing transgenic animals expressing all, or a part, of the nucleic acid molecules and peptides.

The nucleic acid molecules are also useful as hybridization probes for determining the presence, level, form and distribution of nucleic acid expression. Accordingly, the probes can be used to detect the presence of, or to determine levels of, a specific nucleic acid molecule in cells, tissues, and in organisms. The nucleic acid whose level is determined can be DNA or RNA. Accordingly, probes corresponding to the peptides described herein can be used to assess expression and/or gene copy number in a given cell, tissue, or organism. These uses are relevant for diagnosis of disorders involving an increase or decrease in secreted protein expression relative to normal results.

In vitro techniques for detection of mRNA include Northern hybridizations and in situ hybridizations. In vitro techniques for detecting DNA include Southern hybridizations and in situ hybridization.

Probes can be used as a part of a diagnostic test kit for identifying cells or tissues that express a secreted protein, such as by measuring a level of a secreted protein-encoding nucleic acid in a sample of cells from a subject e.g., mRNA or genomic DNA, or determining if a secreted protein gene has been mutated.

Nucleic acid expression assays are useful for drug screening to identify compounds that modulate secreted protein nucleic acid expression.

The invention thus provides a method for identifying a compound that can be used to treat a disorder associated with nucleic acid expression of the secreted protein gene, particularly biological and pathological processes that are mediated by the secreted protein in cells and tissues that express it. The method typically includes assaying the ability of the compound to modulate the expression of the secreted protein nucleic acid and thus identifying a compound that can be used to treat a disorder characterized by undesired secreted protein nucleic acid expression. The assays can be performed in cell-based and cell-free systems. Cell-based assays include cells naturally expressing the secreted protein nucleic acid or recombinant cells genetically engineered to express specific nucleic acid sequences.

Thus, modulators of secreted protein gene expression can be identified in a method wherein a cell is contacted with a candidate compound and the expression of mRNA determined. The level of expression of secreted protein mRNA in the presence of the candidate compound is compared to the level of expression of secreted protein mRNA in the absence of the candidate compound. The candidate compound can then be identified as a modulator of nucleic acid expression based on this comparison and be used, for example to treat a disorder characterized by aberrant nucleic acid expression. When expression of mRNA is statistically significantly greater in the presence of the candidate compound than in its absence, the candidate compound is identified as a stimulator of nucleic acid expression. When nucleic acid expression is statistically significantly less in the presence of the candidate compound than in its absence, the candidate compound is identified as an inhibitor of nucleic acid expression.

The invention further provides methods of treatment, with the nucleic acid as a target, using a compound identified through drug screening as a gene modulator to modulate secreted protein nucleic acid expression in cells and tissues that express the secreted protein. Modulation includes both up-regulation (i.e. activation or agonization) or down-regulation (suppression or antagonization) or nucleic acid expression.

Alternatively, a modulator for secreted protein nucleic acid expression can be a small molecule or drug identified using the screening assays described herein as long as the drug or small molecule inhibits the secreted protein nucleic acid expression in the cells and tissues that express the protein.

The nucleic acid molecules are also useful for monitoring the effectiveness of modulating compounds on the expression or activity of the secreted protein gene in clinical trials or in a treatment regimen. Thus, the gene expression pattern can serve as a barometer for the continuing effectiveness of treatment with the compound, particularly with compounds to which a patient can develop resistance. The gene expression pattern can also serve as a marker indicative of a physiological response of the affected cells to the compound. Accordingly, such monitoring would allow either increased administration of the compound or the administration of alternative compounds to which the patient has not become resistant. Similarly, if the level of nucleic acid expression falls below a desirable level, administration of the compound could be commensurately decreased.

The nucleic acid molecules are also useful in diagnostic assays for qualitative changes in secreted protein nucleic acid expression, and particularly in qualitative changes that lead to pathology. The nucleic acid molecules can be used to detect mutations in secreted protein genes and gene expression products such as mRNA. The nucleic acid molecules can be used as hybridization probes to detect naturally occurring genetic mutations in the secreted protein gene and thereby to determine whether a subject with the mutation is at risk for a disorder caused by the mutation. Mutations include deletion, addition, or substitution of one or more nucleotides in the gene, chromosomal rearrangement, such as inversion or transposition, modification of genomic DNA, such as aberrant methylation patterns or changes in gene copy number, such as amplification. Detection of a mutated form of the secreted protein gene associated with a dysfunction provides a diagnostic tool for an active disease or susceptibility to disease when the disease results from overexpression, underexpression, or altered expression of a secreted protein.

Individuals carrying mutations in the secreted protein gene can be detected at the nucleic acid level by a variety of techniques. Genomic DNA can be analyzed directly or can be amplified by using PCR prior to analysis. RNA or cDNA can be used in the same way. In some uses, detection of the mutation involves the use of a probe/primer in a polymerase chain reaction (PCR) (see, e.g. U.S. Pat. Nos. 4,683,195 and 4,683,202), such as anchor PCR or RACE PCR, or, alternatively, in a ligation chain reaction (LCR) (see, e.g., Landegran et al., *Science* 241:1077–1080 (1988); and Nakazawa et al., *PNAS* 91:360–364 (1994)), the latter of which can be particularly useful for detecting point mutations in the gene (see Abravaya et al., *Nucleic Acids Res.* 23:675–682 (1995)). This method can include the steps of collecting a sample of cells from a patient, isolating nucleic acid (e.g., genomic, mRNA or both) from the cells of the sample, contacting the nucleic acid sample with one or more primers which specifically hybridize to a gene under conditions such that hybridization and amplification of the gene (if present) occurs, and detecting the presence or absence of an amplification product, or detecting the size of the amplification product and comparing the length to a control sample. Deletions and insertions can be detected by a change in size of the amplified product compared to the normal genotype. Point mutations can be identified by hybridizing amplified DNA to normal RNA or antisense DNA sequences.

Alternatively, mutations in a secreted protein gene can be directly identified, for example, by alterations in restriction enzyme digestion patterns determined by gel electrophoresis.

Further, sequence-specific ribozymes (U.S. Pat. No. 5,498,531) can be used to score for the presence of specific mutations by development or loss of a ribozyme cleavage site. Perfectly matched sequences can be distinguished from mismatched sequences by nuclease cleavage digestion assays or by differences in melting temperature.

Sequence changes at specific locations can also be assessed by nuclease protection assays such as RNase and S1 protection or the chemical cleavage method. Furthermore, sequence differences between a mutant secreted protein gene and a wild-type gene can be determined by direct DNA sequencing. A variety of automated sequencing procedures can be utilized when performing the diagnostic assays (Naeve, C. W., (1995) *Biotechniques* 19:448), including sequencing by mass spectrometry (see, e.g., PCT International Publication No. WO 94/16101; Cohen et al., *Adv. Chromatogr.* 36:127–162 (1996); and Griffin et al., *Appl. Biochem. Biotechnol.* 38:147–159 (1993)).

Other methods for detecting mutations in the gene include methods in which protection from cleavage agents is used to detect mismatched bases in RNA/RNA or RNA/DNA duplexes (Myers et al., *Science* 230:1242 (1985)); Cotton et al., *PNAS* 85:4397 (1988); Saleeba et al., *Meth. Enzymol.* 217:286–295 (1992)), electrophoretic mobility of mutant and wild type nucleic acid is compared (Orita et al., *PNAS* 86:2766 (1989); Cotton et al., *Mutat. Res.* 285:125–144 (1993); and Hayashi et al., *Genet. Anal. Tech. Appl.,* 9:73–79 (1992)), and movement of mutant or wild-type fragments in polyacrylamide gels containing a gradient of denaturant is assayed using denaturing gradient gel electrophoresis (Myers et al., *Nature* 313:495 (1985)). Examples of other techniques for detecting point mutations include selective oligonucleotide hybridization, selective amplification, and selective primer extension.

The nucleic acid molecules are also useful for testing an individual for a genotype that while not necessarily causing the disease, nevertheless affects the treatment modality. Thus, the nucleic acid molecules can be used to study the relationship between an individual's genotype and the individual's response to a compound used for treatment (pharmacogenomic relationship). Accordingly, the nucleic acid molecules described herein can be used to assess the mutation content of the secreted protein gene in an individual in order to select an appropriate compound or dosage regimen for treatment.

Thus nucleic acid molecules displaying genetic variations that affect treatment provide a diagnostic target that can be used to tailor treatment in an individual. Accordingly, the production of recombinant cells and animals containing these polymorphisms allow effective clinical design of treatment compounds and dosage regimens.

The nucleic acid molecules are thus useful as antisense constructs to control secreted protein gene expression in cells, tissues, and organisms. A DNA antisense nucleic acid molecule is designed to be complementary to a region of the gene involved in transcription, preventing transcription and hence production of secreted protein. An antisense RNA or DNA nucleic acid molecule would hybridize to the mRNA and thus block translation of mRNA into secreted protein.

Alternatively, a class of antisense molecules can be used to inactivate mRNA in order to decrease expression of secreted protein nucleic acid. Accordingly, these molecules can treat a disorder characterized by abnormal or undesired secreted protein nucleic acid expression. This technique involves cleavage by means of ribozymes containing nucleotide sequences complementary to one or more regions in the mRNA that attenuate the ability of the mRNA to be translated. Possible regions include coding regions and particularly coding regions corresponding to the catalytic and other functional activities of the secreted protein, such as substrate binding.

The nucleic acid molecules also provide vectors for gene therapy in patients containing cells that are aberrant in secreted protein gene expression. Thus, recombinant cells, which include the patient's cells that have been engineered ex vivo and returned to the patient, are introduced into an individual where the cells produce the desired secreted protein to treat the individual.

The invention also encompasses kits for detecting the presence of a secreted protein nucleic acid in a biological sample. For example, the kit can comprise reagents such as a labeled or labelable nucleic acid or agent capable of detecting secreted protein nucleic acid in a biological sample; means for determining the amount of secreted protein nucleic acid in the sample; and means for comparing the amount of secreted protein nucleic acid in the sample with a standard. The compound or agent can be packaged in a suitable container. The kit can further comprise instructions for using the kit to detect secreted protein mRNA or DNA.

Nucleic Acid Arrays

The present invention further provides nucleic acid detection kits, such as arrays or microarrays of nucleic acid molecules that are based on the sequence information provided in FIGS. 1 and 3 (SEQ ID NOS:1 and 3).

As used herein "Arrays" or "Microarrays" refers to an array of distinct polynucleotides or oligonucleotides synthesized on a substrate, such as paper, nylon or other type of membrane, filter, chip, glass slide, or any other suitable solid support. In one embodiment, the microarray is prepared and used according to the methods described in U.S. Pat. No. 5,837,832, Chee et al., PCT application WO95/11995 (Chee et al.), Lockhart, D. J. et al. (1996; Nat. Biotech. 14: 1675–1680) and Schena, M. et al. (1996; Proc. Natl. Acad. Sci. 93: 10614–10619), all of which are incorporated herein in their entirety by reference. In other embodiments, such arrays are produced by the methods described by Brown et al., U.S. Pat. No. 5,807,522.

The microarray or detection kit is preferably composed of a large number of unique, single-stranded nucleic acid sequences, usually either synthetic antisense oligonucleotides or fragments of cDNAs, fixed to a solid support. The oligonucleotides are preferably about 6–60 nucleotides in length, more preferably 15–30 nucleotides in length, and most preferably about 20–25 nucleotides in length. For a certain type of microarray or detection kit, it may be preferable to use oligonucleotides that are only 7–20 nucleotides in length. The microarray or detection kit may contain oligonucleotides that cover the known 5', or 3', sequence, sequential oligonucleotides which cover the full length sequence; or unique oligonucleotides selected from particular areas along the length of the sequence. Polynucleotides used in the microarray or detection kit may be oligonucleotides that are specific to a gene or genes of interest.

In order to produce oligonucleotides to a known sequence for a microarray or detection kit, the gene(s) of interest (or an ORF identified from the contigs of the present invention) is typically examined using a computer algorithm which starts at the 5' or at the 3' end of the nucleotide sequence. Typical algorithms will then identify oligomers of defined length that are unique to the gene, have a GC content within a range suitable for hybridization, and lack predicted secondary structure that may interfere with hybridization. In certain situations it may be appropriate to use pairs of oligonucleotides on a microarray or detection kit. The "pairs" will be identical, except for one nucleotide that preferably is located in the center of the sequence. The second oligonucleotide in the pair (mismatched by one) serves as a control. The number of oligonucleotide pairs may range from two to one million. The oligomers are synthesized at designated areas on a substrate using a light-directed chemical process. The substrate may be paper, nylon or other type of membrane, filter, chip, glass slide or any other suitable solid support.

In another aspect, an oligonucleotide may be synthesized on the surface of the substrate by using a chemical coupling procedure and an ink jet application apparatus, as described in PCT application WO95/251116 (Baldeschweiler et al.) which is incorporated herein in its entirety by reference. In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array, such as those described above, may be produced by hand or by using available devices (slot blot or dot blot apparatus), materials (any suitable solid support), and machines (including robotic instruments), and may contain 8, 24, 96, 384, 1536, 6144 or more oligonucleotides, or any other number between two and one million which lends itself to the efficient use of commercially available instrumentation.

In order to conduct sample analysis using a microarray or detection kit, the RNA or DNA from a biological sample is made into hybridization probes. The mRNA is isolated, and cDNA is produced and used as a template to make antisense RNA (aRNA). The aRNA is amplified in the presence of fluorescent nucleotides, and labeled probes are incubated with the microarray or detection kit so that the probe sequences hybridize to complementary oligonucleotides of the microarray or detection kit. Incubation conditions are adjusted so that hybridization occurs with precise complementary matches or with various degrees of less complementarity. After removal of nonhybridized probes, a scanner is used to determine the levels and patterns of fluorescence. The scanned images are examined to determine degree of complementarity and the relative abundance of each oligonucleotide sequence on the microarray or detection kit. The biological samples may be obtained from any bodily fluids (such as blood, urine, saliva, phlegm, gastric juices, etc.), cultured cells, biopsies, or other tissue preparations. A detection system may be used to measure the absence, presence, and amount of hybridization for all of the distinct sequences simultaneously. This data may be used for large-scale correlation studies on the sequences, expression patterns, mutations, variants, or polymorphisms among samples.

Using such arrays, the present invention provides methods to identify the expression of the secreted proteins/peptides of the present invention. In detail, such methods comprise incubating a test sample with one or more nucleic acid molecules and assaying for binding of the nucleic acid molecule with components within the test sample. Such assays will typically involve arrays comprising many genes, at least one of which is a gene of the present invention and or alleles of the secreted protein gene of the present invention.

Conditions for incubating a nucleic acid molecule with a test sample vary. Incubation conditions depend on the format employed in the assay, the detection methods employed, and the type and nature of the nucleic acid molecule used in the assay. One skilled in the art will recognize that any one of the commonly available hybridization, amplification or array assay formats can readily be adapted to employ the novel fragments of the Human genome disclosed herein. Examples of such assays can be found in Chard, T, *An Introduction to Radioimmunoassay and Related Techniques,* Elsevier Science Publishers, Amsterdam, The Netherlands (1986); Bullock, G. R. et al., *Techniques in Immunocytochemistry,* Academic Press, Orlando, Fla. Vol. 1 (1982), Vol. 2 (1983), Vol. 3 (1985); Tijssen, P., *Practice and Theory of Enzyme Immunoassays: Laboratory Techniques in Biochemistry and Molecular Biology,* Elsevier Science Publishers, Amsterdam, The Netherlands (1985).

The test samples of the present invention include cells, protein or membrane extracts of cells. The test sample used in the above-described method will vary based on the assay format, nature of the detection method and the tissues, cells or extracts used as the sample to be assayed. Methods for preparing nucleic acid extracts or of cells are well known in the art and can be readily be adapted in order to obtain a sample that is compatible with the system utilized.

In another embodiment of the present invention, kits are provided which contain the necessary reagents to carry out the assays of the present invention.

Specifically, the invention provides a compartmentalized kit to receive, in close confinement, one or more containers which comprises: (a) a first container comprising one of the nucleic acid molecules that can bind to a fragment of the Human genome disclosed herein; and (b) one or more other containers comprising one or more of the following: wash reagents, reagents capable of detecting presence of a bound nucleic acid.

In detail, a compartmentalized kit includes any kit in which reagents are contained in separate containers. Such containers include small glass containers, plastic containers, strips of plastic, glass or paper, or arraying material such as silica. Such containers allows one to efficiently transfer reagents from one compartment to another compartment such that the samples and reagents are not cross-contaminated, and the agents or solutions of each container can be added in a quantitative fashion from one compartment to another. Such containers will include a container which will accept the test sample, a container which contains the nucleic acid probe, containers which contain wash reagents (such as phosphate buffered saline, Tris-buffers, etc.), and containers which contain the reagents used to detect the bound probe. One skilled in the art will readily recognize that the previously unidentified secreted protein gene of the present invention can be routinely identified using the sequence information disclosed herein can be readily incorporated into one of the established kit formats which are well known in the art, particularly expression arrays.

Vectors/Host Cells

The invention also provides vectors containing the nucleic acid molecules described herein. The term "vector" refers to a vehicle, preferably a nucleic acid molecule, which can transport the nucleic acid molecules. When the vector is a nucleic acid molecule, the nucleic acid molecules are covalently linked to the vector nucleic acid. With this aspect of the invention, the vector includes a plasmid, single or double stranded phage, a single or double stranded RNA or DNA viral vector, or artificial chromosome, such as a BAC, PAC, YAC, OR MAC.

A vector can be maintained in the host cell as an extra-chromosomal element where it replicates and produces additional copies of the nucleic acid molecules. Alternatively, the vector may integrate into the host cell genome and produce additional copies of the nucleic acid molecules when the host cell replicates.

The invention provides vectors for the maintenance (cloning vectors) or vectors for expression (expression vectors) of the nucleic acid molecules. The vectors can function in prokaryotic or eukaryotic cells or in both (shuttle vectors).

Expression vectors contain cis-acting regulatory regions that are operably linked in the vector to the nucleic acid molecules such that transcription of the nucleic acid molecules is allowed in a host cell. The nucleic acid molecules can be introduced into the host cell with a separate nucleic acid molecule capable of affecting transcription. Thus, the second nucleic acid molecule may provide a trans-acting factor interacting with the cis-regulatory control region to allow transcription of the nucleic acid molecules from the vector. Alternatively, a trans-acting factor may be supplied by the host cell. Finally, a trans-acting factor can be produced from the vector itself. It is understood, however, that in some embodiments, transcription and/or translation of the nucleic acid molecules can occur in a cell-free system.

The regulatory sequence to which the nucleic acid molecules described herein can be operably linked include promoters for directing mRNA transcription. These include, but are not limited to, the left promoter from bacteriophage λ, the lac, TRP, and TAC promoters from *E. Coli,* the early and late promoters from SV40, the CMV immediate early promoter, the adenovirus early and late promoters, and retrovirus long-terminal repeats.

In addition to control regions that promote transcription, expression vectors may also include regions that modulate transcription, such as repressor binding sites and enhancers. Examples include the SV40 enhancer, the cytomegalovirus immediate early enhancer, polyoma enhancer, adenovirus enhancers, and retrovirus LTR enhancers.

In addition to containing sites for transcription initiation and control, expression vectors can also contain sequences necessary for transcription termination and, in the transcribed region a ribosome binding site for translation. Other regulatory control elements for expression include initiation and termination codons as well as polyadenylation signals. The person of ordinary skill in the art would be aware of the numerous regulatory sequences that are useful in expression vectors. Such regulatory sequences are described, for example, in Sambrook et al., *Molecular Cloning: A Laboratory Manual. 2nd. ed.,* Cold Spring Harbor Laboratory Press, Cold Spring Harbor, N.Y., (1989).

A variety of expression vectors can be used to express a nucleic acid molecule. Such vectors include chromosomal, episomal, and virus-derived vectors, for example vectors derived from bacterial plasmids, from bacteriophage, from yeast episomes, from yeast chromosomal elements, including yeast artificial chromosomes, from viruses such as baculoviruses, papovaviruses such as SV40, Vaccinia viruses, adenoviruses, poxviruses, pseudorabies viruses, and retroviruses. Vectors may also be derived from combinations of these sources such as those derived from plasmid and bacteriophage genetic elements, e.g. cosmids and phagemids. Appropriate cloning and expression vectors for prokaryotic and eukaryotic hosts are described in Sambrook et al, *Molecular Cloning: A Laboratory Manual. 2nd. ed., Cold Spring Harbor Laboratory Press, Cold Spring Harbor, N.Y.,* (1989).

The regulatory sequence may provide constitutive expression in one or more host cells (i.e. tissue specific) or may provide for inducible expression in one or more cell types such as by temperature, nutrient additive, or exogenous factor such as a hormone or other ligand. A variety of vectors providing for constitutive and inducible expression in prokaryotic and eukaryotic hosts are well known to those of ordinary skill in the art.

The nucleic acid molecules can be inserted into the vector nucleic acid by well-known methodology. Generally, the DNA sequence that will ultimately be expressed is joined to an expression vector by cleaving the DNA sequence and the expression vector with one or more restriction enzymes and then ligating the fragments together. Procedures for restriction enzyme digestion and ligation are well known to those of ordinary skill in the art.

The vector containing the appropriate nucleic acid molecule can be introduced into an appropriate host cell for propagation or expression using well-known techniques. Bacterial cells include, but are not limited to, *E. coli,* Streptomyces, and *Salmonella typhimurium.* Eukaryotic cells include, but are not limited to, yeast, insect cells such as Drosophila, animal cells such as COS and CHO cells, and plant cells.

As described herein, it may be desirable to express the peptide as a fusion protein. Accordingly, the invention provides fusion vectors that allow for the production of the peptides. Fusion vectors can increase the expression of a recombinant protein, increase the solubility of the recombinant protein, and aid in the purification of the protein by acting for example as a ligand for affinity purification. A proteolytic cleavage site may be introduced at the junction of the fusion moiety so that the desired peptide can ultimately be separated from the fusion moiety. Proteolytic enzymes include, but are not limited to, factor Xa, thrombin, and enterokinase. Typical fusion expression vectors include pGEX (Smith et al., *Gene* 67:31–40 (1988)), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. Examples of suitable inducible non-fusion *E. coli* expression vectors include pTrc (Amann et al., *Gene* 69:301–315 (1988)) and pET 11d (Studier et al., *Gene Expression Technology: Methods in Enzymology* 185:60–89 (1990)).

Recombinant protein expression can be maximized in host bacteria by providing a genetic background wherein the host cell has an impaired capacity to proteolytically cleave the recombinant protein. (Gottesman, S., *Gene Expression Technology: Methods in Enzymology* 185, Academic Press, San Diego, Calif. (1990)119–128). Alternatively, the sequence of the nucleic acid molecule of interest can be altered to provide preferential codon usage for a specific host cell, for example *E. coli.* (Wada et al., *Nucleic Acids Res.* 20:2111–2118 (1992)).

The nucleic acid molecules can also be expressed by expression vectors that are operative in yeast. Examples of vectors for expression in yeast e.g., *S. cerevisiae* include pYepSec1 (Baldari, et al., *EMBO J.* 6:229–234 (1987)), pMFa (Kujan et al., *Cell* 30:933–943(1982)), pJRY88 (Schultz et al., *Gene* 54:113–123 (1987)), and pYES2 (Invitrogen Corporation, San Diego, Calif.).

The nucleic acid molecules can also be expressed in insect cells using, for example, baculovirus expression vectors. Baculovirus vectors available for expression of proteins in cultured insect cells (e.g., Sf9 cells) include the pAc series (Smith et al., *Mol. Cell Biol.* 3:2156–2165 (1983)) and the pVL series (Lucklow et al., *Virology* 170:31–39 (1989)).

In certain embodiments of the invention, the nucleic acid molecules described herein are expressed in mammalian cells using mammalian expression vectors. Examples of mammalian expression vectors include pCDM8 (Seed, B. *Nature* 329:840(1987)) and pMT2PC (Kaufman et al., *EMBO J.* 6:187–195 (1987)).

The expression vectors listed herein are provided by way of example only of the well-known vectors available to those of ordinary skill in the art that would be useful to express the nucleic acid molecules. The person of ordinary skill in the art would be aware of other vectors suitable for maintenance propagation or expression of the nucleic acid molecules described herein. These are found for example in Sambrook, J., Fritsh, E. F., and Maniatis, T. *Molecular Cloning: A Laboratory Manual. 2nd, ed., Cold Spring Harbor Laboratory,* Cold Spring Harbor Laboratory Press, Cold Spring Harbor, N.Y., 1989.

The invention also encompasses vectors in which the nucleic acid sequences described herein are cloned into the vector in reverse orientation, but operably linked to a regulatory sequence that permits transcription of antisense RNA. Thus, an antisense transcript can be produced to all, or to a portion, of the nucleic acid molecule sequences described herein, including both coding and non-coding regions. Expression of this antisense RNA is subject to each of the parameters described above in relation to expression of the sense RNA (regulatory sequences, constitutive or inducible expression, tissue-specific expression).

The invention also relates to recombinant host cells containing the vectors described herein. Host cells therefore include prokaryotic cells, lower eukaryotic cells such as yeast, other eukaryotic cells such as insect cells, and higher eukaryotic cells such as mammalian cells.

The recombinant host cells are prepared by introducing the vector constructs described herein into the cells by techniques readily available to the person of ordinary skill in the art. These include, but are not limited to, calcium phosphate transfection, DEAE-dextran-mediated transfection, cationic lipid-mediated transfection, electroporation, transduction, infection, lipofection, and other techniques such as those found in Sambrook, et al. (*Molecular Cloning: A Laboratory Manual. 2nd, ed., Cold Spring Harbor Laboratory,* Cold Spring Harbor Laboratory Press, Cold Spring Harbor, N.Y., 1989).

Host cells can contain more than one vector. Thus, different nucleotide sequences can be introduced on different vectors of the same cell. Similarly, the nucleic acid molecules can be introduced either alone or with other nucleic acid molecules that are not related to the nucleic acid molecules such as those providing trans-acting factors for expression vectors. When more than one vector is introduced into a cell, the vectors can be introduced independently, co-introduced or joined to the nucleic acid molecule vector.

In the case of bacteriophage and viral vectors, these can be introduced into cells as packaged or encapsulated virus by standard procedures for infection and transduction. Viral vectors can be replication-competent or replication-defective. In the case in which viral replication is defective, replication will occur in host cells providing functions that complement the defects.

Vectors generally include selectable markers that enable the selection of the subpopulation of cells that contain the recombinant vector constructs. The marker can be contained in the same vector that contains the nucleic acid molecules described herein or may be on a separate vector. Markers include tetracycline or ampicillin-resistance genes for prokaryotic host cells and dihydrofolate reductase or neomycin resistance for eukaryotic host cells. However, any marker that provides selection for a phenotypic trait will be effective.

While the mature proteins can be produced in bacteria, yeast, mammalian cells, and other cells under the control of the appropriate regulatory sequences, cell-free transcription and translation systems can also be used to produce these proteins using RNA derived from the DNA constructs described herein.

Where secretion of the peptide is desired, which is difficult to achieve with multi-transmembrane domain containing proteins such as kinases, appropriate secretion signals are incorporated into the vector. The signal sequence can be endogenous to the peptides or heterologous to these peptides.

Where the peptide is not secreted into the medium, which is typically the case with kinases, the protein can be isolated from the host cell by standard disruption procedures, including freeze thaw, sonication, mechanical disruption, use of lysing agents and the like. The peptide can then be recovered and purified by well-known purification methods including ammonium sulfate precipitation, acid extraction, anion or cationic exchange chromatography, phosphocellulose chromatography, hydrophobic-interaction chromatography, affinity chromatography, hydroxylapatite chromatography, lectin chromatography, or high performance liquid chromatography.

It is also understood that depending upon the host cell in recombinant production of the peptides described herein, the peptides can have various glycosylation patterns, depending upon the cell, or maybe non-glycosylated as when produced in bacteria. In addition, the peptides may include an initial modified methionine in some cases as a result of a host-mediated process.

Uses of Vectors and Host Cells

The recombinant host cells expressing the peptides described herein have a variety of uses. First, the cells are useful for producing a secreted protein or peptide that can be further purified to produce desired amounts of secreted protein or fragments. Thus, host cells containing expression vectors are useful for peptide production.

Host cells are also useful for conducting cell-based assays involving the secreted protein or secreted protein fragments, such as those described above as well as other formats known in the art. Thus, a recombinant host cell expressing a native secreted protein is useful for assaying compounds that stimulate or inhibit secreted protein function.

Host cells are also useful for identifying secreted protein mutants in which these functions are affected. If the mutants naturally occur and give rise to a pathology, host cells containing the mutations are useful to assay compounds that have a desired effect on the mutant secreted protein (for example, stimulating or inhibiting function) which may not be indicated by their effect on the native secreted protein.

Genetically engineered host cells can be further used to produce non-human transgenic animals. A transgenic animal is preferably a mammal, for example a rodent, such as a rat or mouse, in which one or more of the cells of the animal include a transgene. A transgene is exogenous DNA which is integrated into the genome of a cell from which a transgenic animal develops and which remains in the genome of the mature animal in one or more cell types or tissues of the transgenic animal. These animals are useful for studying the function of a secreted protein and identifying and evaluating modulators of secreted protein activity. Other examples of transgenic animals include non-human primates, sheep, dogs, cows, goats, chickens, and amphibians.

A transgenic animal can be produced by introducing nucleic acid into the male pronuclei of a fertilized oocyte, e.g., by microinjection, retroviral infection, and allowing the oocyte to develop in a pseudopregnant female foster animal. Any of the secreted protein nucleotide sequences can be introduced as a transgene into the genome of a non-human animal, such as a mouse.

Any of the regulatory or other sequences useful in expression vectors can form part of the transgenic sequence. This includes intronic sequences and polyadenylation signals, if not already included. A tissue-specific regulatory sequence(s) can be operably linked to the transgene to direct expression of the secreted protein to particular cells.

Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo,* (Cold Spring Harbor Laboratory Press, Cold Spring Harbor, N.Y., 1986). Similar methods are used for production of other transgenic animals. A transgenic founder animal can be identified based upon the presence of the transgene in its genome and/or expression of transgenic mRNA in tissues or cells of the animals. A transgenic founder animal can then be used to breed additional animals carrying the transgene. Moreover, transgenic animals carrying a transgene can further be bred to other transgenic animals carrying other transgenes. A transgenic animal also includes animals in which the entire animal or tissues in the animal have been produced using the homologously recombinant host cells described herein.

In another embodiment, transgenic non-human animals can be produced which contain selected systems that allow for regulated expression of the transgene. One example of such a system is the cre/loxP recombinase system of bacteriophage P1. For a description of the cre/loxP recombinase system, see, e.g., Lakso et al. PNAS 89:6232–6236 (1992). Another example of a recombinase system is the FLP recombinase system of S. cerevisiae (O'Gorman et al. Science 251:1351–1355 (1991). If a cre/loxP recombinase system is used to regulate expression of the transgene, animals containing transgenes encoding both the Cre recombinase and a selected protein is required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. Nature 385:810–813 (1997) and PCT International Publication Nos. WO 97/07668 and WO 97/07669. In brief, a cell, e.g., a somatic cell, from the transgenic animal can be isolated and induced to exit the growth cycle and enter $G_o$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyst and then transferred to pseudopregnant female foster animal. The offspring born of this female foster animal will be a clone of the animal from which the cell, e.g., the somatic cell, is isolated.

Transgenic animals containing recombinant cells that express the peptides described herein are useful to conduct the assays described herein in an in vivo context. Accordingly, the various physiological factors that are present in vivo and that could effect substrate binding, secreted protein activation, and signal transduction, may not be evident from in vitro cell-free or cell-based assays. Accordingly, it is useful to provide non-human transgenic animals to assay in vivo secreted protein function, including substrate interaction, the effect of specific mutant secreted proteins on secreted protein function and substrate interaction, and the effect of chimeric secreted proteins. It is also possible to assess the effect of null mutations, that is, mutations that substantially or completely eliminate one or more secreted protein functions.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the above-described modes for carrying out the invention which are obvious to those skilled in the field of molecular biology or related fields are intended to be within the scope of the following claims.

That which is claimed is:

1. An isolated polypeptide having an amino acid sequence consisting of SEQ ID NO:2.

2. An isolated lactate dehydrogenase having an amino acid sequence comprising SEQ ID NO:2.

3. A composition comprising the polypeptide of claim 1 and a carrier.

4. A composition comprising the lactate dehydrogenase of claim 2 and a carrier.

* * * * *